US009783846B2

United States Patent
Olek

(10) Patent No.: US 9,783,846 B2
(45) Date of Patent: Oct. 10, 2017

(54) **DETECTION OF IMMUNE CELLS, IN PARTICULAR T CELLS THROUGH DNA-METHYLATION ANALYSIS OF THE GENES *CCR6* AND *BLR1***

(75) Inventor: Sven Olek, Berlin (DE)

(73) Assignee: EPIONTIS GMBH, Berlin (DE)

( * ) Notice: Subject to any disclaimer, the term of this patent is extended or adjusted under 35 U.S.C. 154(b) by 495 days.

(21) Appl. No.: 13/636,556

(22) PCT Filed: Apr. 29, 2011

(86) PCT No.: PCT/EP2011/056871
§ 371 (c)(1),
(2), (4) Date: Dec. 3, 2012

(87) PCT Pub. No.: WO2011/135088
PCT Pub. Date: Nov. 3, 2011

(65) Prior Publication Data
US 2013/0089861 A1 Apr. 11, 2013

Related U.S. Application Data

(60) Provisional application No. 61/329,229, filed on Apr. 29, 2010.

(51) Int. Cl.
*C12Q 1/68* (2006.01)
(52) U.S. Cl.
CPC ........... *C12Q 1/686* (2013.01); *C12Q 1/6876* (2013.01); *C12Q 1/6883* (2013.01); *C12Q 1/6869* (2013.01); *C12Q 2523/125* (2013.01); *C12Q 2600/154* (2013.01)

(58) Field of Classification Search
None
See application file for complete search history.

(56) References Cited

U.S. PATENT DOCUMENTS

2005/0227265 A1* 10/2005 Barany et al. .................... 435/6

OTHER PUBLICATIONS

Baron, Udo et al., "DNA demethylation in the human FOXP3 locus discriminates regulatory T cells from activated FOXP3+ conventional T cells", *European Journal of Immunology*, Sep. 2007, vol. 37, No. 9, pp. 2378-2389, XP002639439.

(Continued)

*Primary Examiner* — Joseph G Dauner
(74) *Attorney, Agent, or Firm* — Saliwanchik, Lloyd & Eisenschenk

(57) ABSTRACT

The present invention relates to a method, in particular an in vitro method, for identifying certain immune cells of a mammal, comprising analyzing the methylation status of at least one CpG position in the gene CCR6 and/or BLR1 or an orthologous or paralogous gene thereof, and the use of DNA-methylation analysis of the genes of the proteins CCR6 and/or BLR1 for a detection and quality assurance and control of certain immune cells. In particular, the present invention relates to analyzing the methylation status of at least one CpG position in the gene CCR6 in T cells. Furthermore, the present invention relates to a kit for performing the above methods, as well as to respective uses.

6 Claims, 13 Drawing Sheets
(13 of 13 Drawing Sheet(s) Filed in Color)

(56) References Cited

OTHER PUBLICATIONS

Baron, Udo et al., "Supporting information: DNA demethylation in the human FOXP3 locus discriminates regulatory T cells from activated FOXP+ conventional T cells", *European Journal of Immunology*, 2007, XP002644060.

Henneken, Maren et al., "Differential expression of chemokine receptors on peripheral blood B cells from patients with rheumatoid arthritis and systemic lupus erythematosus", *Arthritis Research & Therapy*, 2005, vol. 7, No. 5, pp. R1001-R1013, XP002639443.

Hoffmann, Petra et al., "Loss of FOXP3 expression in natural human CD4+CD25+ regulatory T cells upon repetitive in vitro stimulation", *European Journal of Immunology*, Apr. 2009, vol. 39, No. 4, pp. 1088-1097, XP002639445.

Kleinewietfeld, Markus et al., "CCR6 expression defines regulatory effector/memory-like cells within the CD25+CD4+ T-cell subset", *Blood*, Apr. 1, 2005, vol. 105, No. 7, pp. 2877-2886, XP002639442.

Koenen, Hans J.P.M. et al., "Human $CD25^{high}FOXP3^{pos}$ regulatory T cells differentiate into IL-17-producing cells", *Blood*, Sep. 15, 2008, vol. 112, No. 6, pp. 2340-2352, XP002639440.

Mizukami, Takuo et al., "Five azacytidine, a DNA methyltransferase inhibitor, specifically inhibits testicular cord formation and Sertoli cell differentiation in vitro", *Molecular Reproduction and Development*, Jun. 2008, vol. 75, No. 6, pp. 1002-1010, XP002639441.

Polansky, Julia et al., "DNA methylation controls FOXP3 gene expression", *European Journal of Immunology*, Jun. 2008, vol. 38, No. 6, pp. 1654-1663, XP002639446.

Wieczorek, Georg et al., "Quantitative DNA methylation analysis of FOXP3 as a new method for counting regulatory T cells in peripheral blood and solid tissue", *Cancer Research*, Jan. 15, 2009, vol. 69, No. 2, pp. 599-608, XP002639444.

* cited by examiner

Figure 3
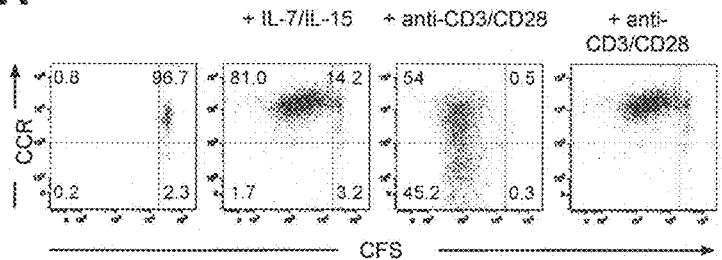
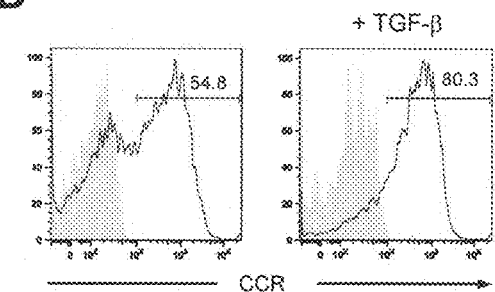
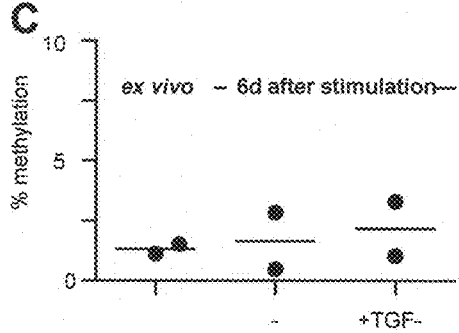
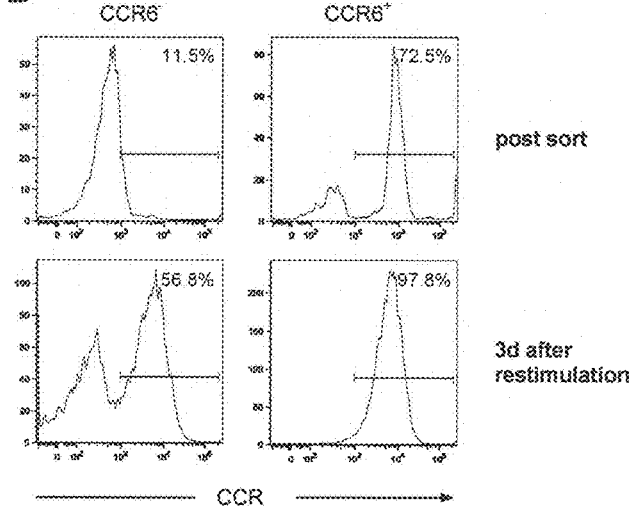

Figure 6

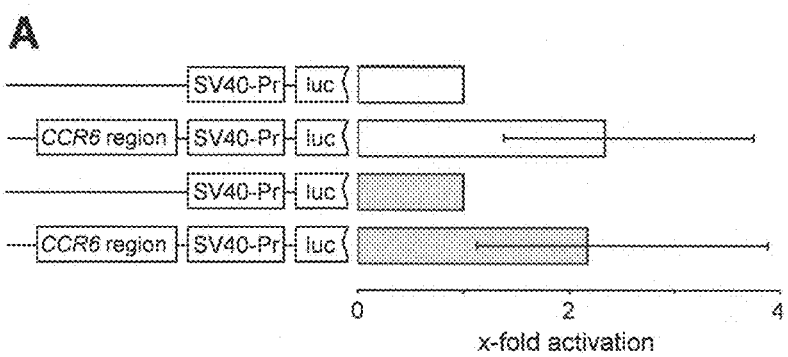

Figure 7 human CCR6 Amplicon

Chromosome 6: 167,535,449 – 167,535,813

```
GCCAGTGGGGTTGAGCAGGACAC  CCTGCTGTGTCTAGCTGGTTCCCCAGAGAGAT   AGG
                   71    RXR    98       106                    GATA
GGTGCGCTCCAGCTTCTCAGGCT    AGCGTGAGGACG GAGCTCAGGGCTCTGC     AGG
    135              AP1*           AHRR  178               193 ETS1
AGCGACCCAGGTGAGGTGT     AAC  GAGCAGAGCTGGCAGCGGGCAGTGGAGCCTCG GG
                RXR    GATA                                    AHRR
CAGCCTGGG  GGGAG  AGTGCACTG  AA TGGAGAAAGTGTGAGTCCATCAGGCTGGCT
      SP1F 277   RBP2      ETS1 RXR              316
GAGAATTGATCACGAACCTATTGTCTGTAAAACTT   TAT    AGACGTGGTTCACAGCAA
                                 FKHD*  NFAT*
    GGTGCGAACAGCCTTGTGATTCTAGGGTTCT         ETS1*
PPAR
```

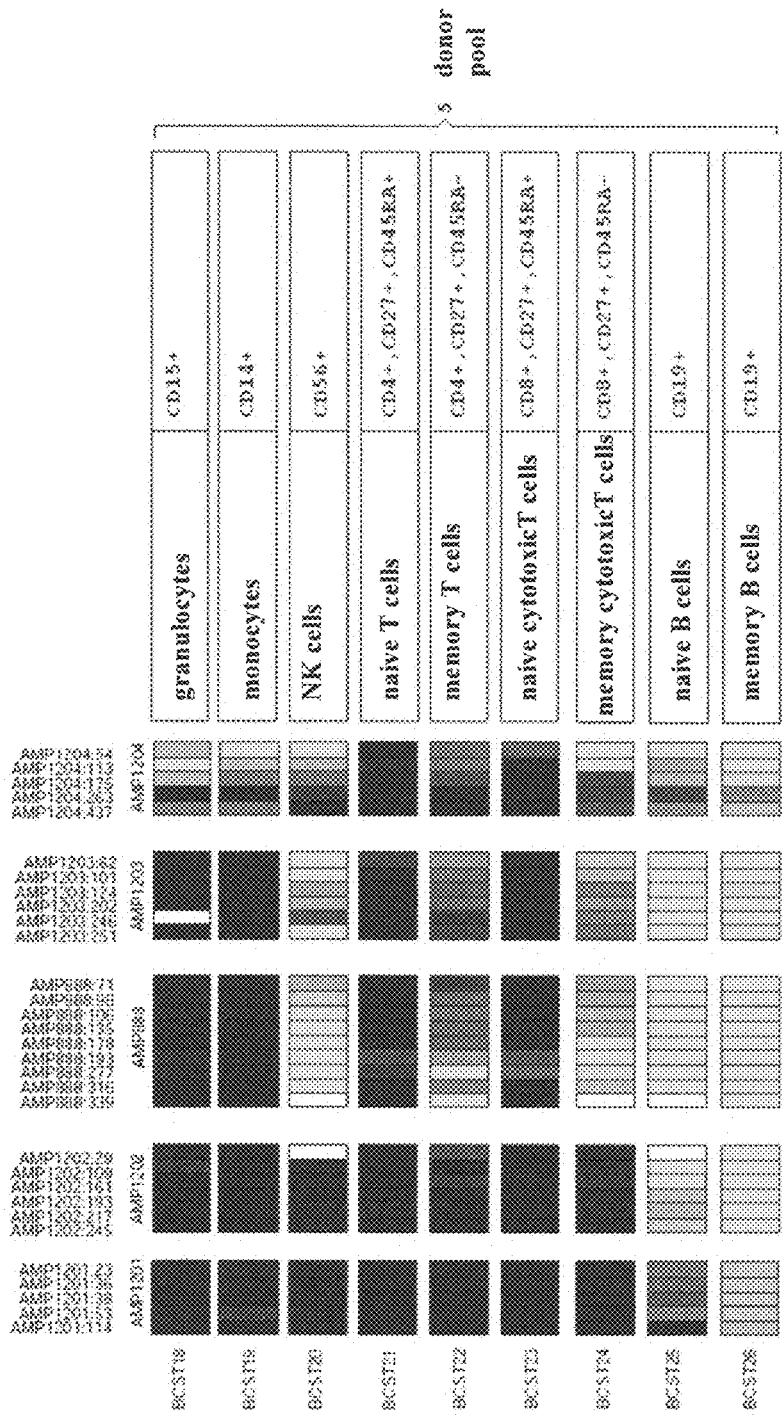

DETECTION OF IMMUNE CELLS, IN PARTICULAR T CELLS THROUGH DNA-METHYLATION ANALYSIS OF THE GENES CCR6 AND BLR1

CROSS REFERENCE TO A RELATED APPLICATION

This application is a National Stage Application of International Application Number PCT/EP2011/056871, filed Apr. 29, 2011; which claims the benefit of U.S. Provisional Application No. 61/329,229, filed Apr. 29, 2010; which are incorporated herein by reference in their entirety.

The present invention relates to a method, in particular an in vitro method, for identifying certain immune cells of a mammal, comprising analysing the methylation status of at least one CpG position in the gene CCR6 and/or BLR1 or an orthologous or paralogous gene thereof, and the use of DNA-methylation analysis of the genes of the proteins CCR6 and/or BLR1 for a detection and quality assurance and control of certain immune cells. In particular, the present invention relates to analysing the methylation status of at least one CpG position in the gene CCR6 in T cells. Furthermore, the present invention relates to a kit for performing the above methods, as well as to respective uses.

For the purpose of the present invention, all references as cited herein as well as the sequence listing are incorporated by reference in their entireties.

BACKGROUND OF THE INVENTION

The Burkitt's lymphoma receptor 1 (BLR1) gene—also known as Chemokine (C-X-C motif) receptor 5 (CXCR5)—was identified initially in Burkitt lymphoma cells has been the first member of the superfamily of G-protein-coupled receptors with a lymphocyte specific expression pattern. BLR1 shows significant relationship to receptors for chemokines (IL-8, MIP-1 beta) and neuropeptides. SCID mice in which mature B cell development is severely impaired exhibit a strongly reduced level of Blr1-specific RNA in the spleen. The analysis of murine lymphoid tumor cell lines representing distinct stages of the B cell lineage reveals elevated expression of Blr1 in B cell lymphomas but not in pre-B lymphomas or plasmacytomas. Murine BLR1 may represent a cytokine/neuropeptide receptor exerting regulatory functions on recirculating mature B lymphocytes (Kaiser E, Förster R, Wolf I, Ebensperger C, Kuehl W M, Lipp M. The G protein-coupled receptor BLR1 is involved in murine B cell differentiation and is also expressed in neuronal tissues. Eur J. Immunol. 1993 October; 23(10): 2532-9; Förster R, Wolf I, Kaiser E, Lipp M. Selective expression of the murine homologue of the G-protein-coupled receptor BLR1 in B cell differentiation, B cell neoplasia and defined areas of the cerebellum. Cell Mol Biol (Noisy-le-grand). 1994 May; 40(3):381-7).

Database entry ABK41953 discloses the amino acid sequence of human Burkitt lymphoma receptor 1, GTP binding protein (chemokine (C-X-C motif) receptor 5), database entry EF064770 discloses the nucleotide sequence of human Burkitt lymphoma receptor 1, GTP binding protein (chemokine (C-X-C motif) receptor 5) (BLR1) gene.

WO 99/28468 and U.S. Pat. No. 6,110,695 describe methods and compositions for identifying agents which modulate the interaction of the chemokine receptor Burkitt's Lymphoma Receptor 1 (BLR1) with its ligand, B Lymphocyte Chemoattractant (BLC), and for modulating the interaction of BLR1 and BLC polypeptides. The methods for identifying BLR1:BLC modulators are described as finding particular application in commercial drug screens.

Specific patterns of chemokine receptor expression ensure an orchestrated migration of leukocytes throughout the body, where immune cells home to their target tissues both under steady-state and inflammatory conditions. The chemokine receptor CCR6 is widely expressed on human blood and tissue leukocytes, among them subsets of dendritic cells, CD45RO$^+$ effector/memory T cells, CD25$^{high}$ regulatory T cells (Treg), naive and memory B cells, NKT cells and NK cells (Berahovich R D, Lai N L, Wei Z, Lanier L L, Schall T J. Evidence for NK cell subsets based on chemokine receptor expression. J Immunol. 2006; 177: 7833-7840.). On memory T cells, CCR6 is expressed on a population of auto-reactive IL-10-producing cells (Dieu M C, Vanbervliet B, Vicari A, et al. Selective recruitment of immature and mature dendritic cells by distinct chemokines expressed in different anatomic sites. J Exp Med. 1998; 188:373-386.) and on the majority of skin- and mucosa-homing cells. Several studies have further shown that CCR6 is consistently expressed on inflammatory IL-17-producing CD4$^+$ T cells (Hirota K, Yoshitomi H, Hashimoto M, et al. Preferential recruitment of CCR6-expressing Th17 cells to inflamed joints via CCL20 in rheumatoid arthritis and its animal model. J Exp Med. 2007; 204:2803-2812.) which are involved in a wide array of adverse inflammatory diseases, such as rheumatoid arthritis, psoriatic disease, inflammatory bowel disease or encephalopathies in mice and men (Hirota K, Yoshitomi H, Hashimoto M, et al. Preferential recruitment of CCR6-expressing Th17 cells to inflamed joints via CCL20 in rheumatoid arthritis and its animal model. J Exp Med. 2007; 204:2803-2812. Ruth J H, Shahrara S, Park C C, et al. Role of macrophage inflammatory protein-3alpha and its ligand CCR6 in rheumatoid arthritis. Lab Invest. 2003; 83:579-588. Homey B, Dieu-Nosjean M C, Wiesenborn A, et al. Up-regulation of macrophage inflammatory protein-3 alpha/CCL20 and CC chemokine receptor 6 in psoriasis. J Immunol. 2000; 164:6621-6632. Hedrick M N, Lonsdorf A S, Shirakawa A K, et al. CCR6 is required for IL-23-induced psoriasis-like inflammation in mice. J Clin Invest. 2009; 119:2317-2329. Kaser A, Ludwiczek O, Holzmann S, et al. Increased expression of CCL20 in human inflammatory bowel disease. J Clin Immunol. 2004; 24:74-85. Reboldi A, Coisne C, Baumjohann D, et al. C-C chemokine receptor 6-regulated entry of TH-17 cells into the CNS through the choroid plexus is required for the initiation of EAE. Nat Immunol. 2009; 10:514-523. Varona R, Cadenas V, Flores J, Martinez A C, Marquez G. CCR6 has a non-redundant role in the development of inflammatory bowel disease. Eur J Immunol. 2003; 33:2937-2946. Matsui T, Akahoshi T, Namai R, et al. Selective recruitment of CCR6-expressing cells by increased production of MIP-3 alpha in rheumatoid arthritis. Clin Exp Immunol. 2001; 125:155-161.).

It is widely assumed that differentiation of T cells into specialized memory subsets also involves the acquisition and stable expression of homing- and chemokine receptor repertoires, allowing tissue- or inflammation-specific trafficking of these subsets (Butcher E C, Picker L J. Lymphocyte homing and homeostasis. Science. 1996; 272:60-66.). However, some studies also report a considerable plasticity in the expression of homing receptors. Whether this also applies to the expression of CCR6 is not known. CCR6 expression can be de novo induced on TCR-stimulated naive T cells by a cocktail of pro-inflammatory cytokines in combination with TGF-β (Acosta-Rodriguez E V, Rivino L, Geginat J, et al. Surface phenotype and antigenic specificity of human interleukin 17-producing T helper memory cells. Nat Immunol. 2007; 8:639-646.).

Increasing evidence has been provided in recent years that differentiation of T cells into distinct lineages with stable phenotypes and functions involves epigenetic regulation of critical effector molecules (Ansel K M, Lee D U, Rao A. An epigenetic view of helper T cell differentiation. Nat Immunol. 2003; 4:616-623. Zhu J, Paul W E. CD4 T cells: fates, functions, and faults. Blood. 2008; 112:1557-1569. Wilson C B, Rowell E, Sekimata M. Epigenetic control of T-helper-cell differentiation. Nat Rev Immunol. 2009; 9:91-105.) or lineage-specific transcription factors such as Foxp3 in Treg (Floess S, Freyer J, Siewert C, et al. Epigenetic control of the foxp3 locus in regulatory T cells. PLoS Biol. 2007; 5:e38. Huehn J, Polansky J K, Hamann A. Epigenetic control of FOXP3 expression: the key to a stable regulatory T-cell lineage? Nat Rev Immunol. 2009; 9:83-89. Baron U, Floess S, Wieczorek G, et al. DNA demethylation in the human FOXP3 locus discriminates regulatory T cells from activated FOXP3+ conventional T cells. Eur J. Immunol. 2007; 37:2378-2389.). Only few studies provided evidence that molecules involved in trafficking are subject to epigenetic regulation in T cells (Scotet E, Schroeder S, Lanzavecchia A. Molecular regulation of CC-chemokine receptor 3 expression in human T helper 2 cells. Blood. 2001; 98:2568-2570. Syrbe U, Jennrich S, Schottelius A, Richter A, Radbruch A, Hamann A. Differential regulation of Pselectin ligand expression in naïve versus memory T cells: evidence for epigenetic regulation of involved glycosyltransferase genes. Blood. 2004; 104:3243-3248.) or cancer cells (Sato N, Matsubayashi H, Fukushima N, Goggins M. The chemokine receptor CXCR4 is regulated by DNA methylation in pancreatic cancer. Cancer Biol Ther. 2005; 4:70-76. Mori T, Kim J, Yamano T, et al. Epigenetic up-regulation of C-C chemokine receptor 7 and C-X-C chemokine receptor 4 expression in melanoma cells. Cancer Res. 2005; 65:1800-1807).

Baba et al. (in Baba, M., Imai, T., Nishimura, M., Kakizaki, M., Takagi, S., Hieshima, K., Nomiyama, H. and Yoshie, O. Identification of CCR6, the specific receptor for a novel lymphocyte-directed CC chemokine LARC J. Biol. Chem. 272 (23), 14893-14898 (1997)) describe the identification of CCR6; Database entry NP_004358 discloses the amino acid sequence of human chemokine (C-C motif) receptor 6.

Rubie et al. (in Rubie, C., Oliveira, V., Kempf, K., Wagner, M., Tilton, B., Rau, B., Kruse, B., Konig, J. and Schilling, M. Involvement of chemokine receptor CCR6 in colorectal cancer metastasis Tumour Biol. 27 (3), 166-174 (2006)) propose an association between CCL20/CCR6 expression in human colorectal cancer and the promotion of colorectal liver metastasis. For this, 30 human cancer samples from colorectal tissue, 30 human samples from colorectal liver metastases and the adjacent nontumorous liver tissues were screened using quantitative real-time PCR, Western blot analysis, histochemistry, microdissection and the enzyme-linked immunosorbent assay (ELISA). While an overexpression of all the chemokine receptors was found in CRC, in colorectal liver metastases only the chemokine receptors CXCR4 and CCR6 were significantly upregulated.

WO 03/014153 describes CCR6 as similar to a cellular virus receptors and methods of use for said receptors.

A context between methylation of CCR6 and or BLR1 and certain types of immune cells, in particular T cells, has not been described.

Even though almost all cells in an individual contain the exact same complement of DNA code, higher organisms must impose and maintain different patterns of gene expression in the various tissue types. Most gene regulation is transitory, depending on the current state of the cell and changes in external stimuli. Persistent regulation, on the other hand, is a primary role of epigenetics—heritable regulatory patterns that do not alter the basic genetic coding of the DNA. DNA methylation is the archetypical form of epigenetic regulation; it serves as the stable memory for cells and performs a crucial role in maintaining the long-term identity of various cell types.

The primary target of methylation is the two-nucleotide sequence Cytosine-Guanine (a 'CpG site'); within this context cytosine (C) can undergo a simple chemical modification to become 5-methyl-cytosine. In the human genome, the CG sequence is much rarer than expected except in certain relatively dense clusters called 'CpG islands'. CpG islands are frequently associated with gene promoters, and it has been estimated that more than half of the human genes have CpG islands (Antequera and Bird, Proc Natl Acad Sci USA. 90:11995-9, 1993).

Aberrant methylation of DNA frequently accompanies the transformation from healthy to cancerous cells. Among the observed effects are genome-wide hypomethylation, increased methylation of tumour suppressor genes and hypomethylation of many oncogenes (reviewed by Jones and Laird, Nature Genetics 21:163-167, 1999; Esteller, Oncogene 21:5427-5440, 2002; Laird, Nature Reviews/Cancer 3:253-266, 2003). Methylation profiles have been recognised to be tumour specific (i.e., changes in the methylation pattern of particular genes or even individual CpGs are diagnostic of particular tumour types) and there is now an extensive collection of diagnostic markers for bladder, breast, colon, oesophagus, stomach, liver, lung, and prostate cancers (summarised by Laird, Nature Reviews/Cancer 3:253-266, 2003).

Epigenetic control by methylation is essential for early development including embryogenesis, X-chromosome inactivation and imprinting (monoallelic silencing) of either the paternal or maternal allele (Erlich, J Cellular Chem 88:899-910, 2003). There is also a class of genes that is active in the germ line, but is silenced by methylation in somatic cells (Bird, Genes and Dev 16:6-21, 2002; Li, Nature Reviews/Genetics 3:662-673, 2002).

Tissue-specific methylation also serves in regulating adult cell types/stages, and in some cases a causal relationship between methylation and gene expression has been established. The following is a partial list of genes, for which methylation changes are strongly implicated in controlling gene expression in tissue-specific manner: Lactate dehydrogenase C (testes); Oxytocin receptor (blood & liver); Tyrosine aminotransferase (liver); GFAP (astrocytes); and Leukosialin (leukocytes). In other cases, methylation may be a by-product of some other primary regulation, or it is required to lock the gene in the "off" state (Erlich, J Cellular Chem 88:899-910, 2003). For the present applications (immune cell identification(s)), a causal (biological) relationship is not required, but merely a strong correlation between methylation patterns and cell types.

A previously published example for such a cell type and cell status specific modification of certain gene regions is found during the lineage commitment of T cells to helper T cells (Th1 or Th2). Naïve (unstimulated) $CD4^+$ T cells become activated upon encountering an antigen and can be committed to alternative cell fates through further stimulation by interleukins. The two types of helper T cells show reciprocal patterns of gene expression; Th1 produces Interferon-gamma (IFN-γ) and silences IL-4, while Th2 produces IL-4 and silences IFN-γ (Ansel et al., Nature Immunol 4:616-623, 2003). For both alternative cell fates, the expression of these genes is inversely correlated with methylation of proximal CpG sites. In Th2 and naïve T cells the IFN-γ promoter is methylated, but not in Th1 cells where IFN-γ is expressed (Attwood et al., CMLS 59:241-257, 2002). Conversely, the entire transcribed region of IL-4 becomes demethylated under Th2-inducing conditions, which strongly correlates with efficient transcription of IL-4. In Th1 cells, this extensive demethylation does not occur, rather particular untranscribed regions gradually become heavily methylated and IL-4 is not expressed (Lee et al., Immunity 16:649-660, 2002). Furthermore, Bruniquel and Schwartz (Nat Immunol. 4:235-40, 2003) have demonstrated that in naive T cells, the IL-2 promoter is heavily methylated and inactive, but after activation of the naïve T cell, the IL-2 gene undergoes rapid and specific demethylation at six consecutive CpGs. This alteration in methylation patterns occurs concomitantly with cell differentiation and increased production of the IL-2 product.

It is an object of the present invention to provide an improved method of expression analysis and in particular expression analysis based on DNA methylation analysis of the genes of the proteins CCR6 and/or BLR1 as a superior tool that can supplement or replace conventional methodologies as an indicator of cell type and status in vertebrates, in order to reliably identify certain immune cells, preferably T cells and/or B cells, of a mammal and/or in a mammal, in particular for a detection and quality assurance and control thereof.

SUMMARY OF THE INVENTION

According to a first aspect thereof, the present invention solves the above object by providing a method for identifying BLR1 and/or CCR6 positive immune cells, preferably NK cells, memory T cells, memory cytotoxic T-cells, naïve B cells, or memory B cells of a mammal, most preferred stable activated T cells, comprising analysing the methylation status of at least one CpG position in the gene CCR6 and/or BLR1 or an orthologous or paralogous gene thereof in said mammal.

It was surprisingly found that a CCR6 and/or BLR1 demethylation is indicative for a stable activation of T lymphocytes. As known in the art T cells or T lymphocytes play a central role in cell-mediated immunity and can be distinguished from other lymphocyte types, such as B cells and natural killer cells by the presence of a special receptor on their cell surface called T cell receptors (TCR). The term "activation" is also known to the person of skill, and activation of CD4$^+$ T cells occurs through the engagement of both the T cell receptor and CD28 on the T cell by the major histocompatibility complex peptide and B7 family members on the APC (antigen-presenting cell), respectively. Cytotoxic T cells destroy virally infected cells and tumor cells, and are also implicated in transplant rejection. These cells are also known as CD8$^+$ T cells since they express the CD8 glycoprotein at their surface. The activation of cytotoxic T cells is dependent on several simultaneous interactions between molecules expressed on the surface of the T cell and molecules on the surface of the APC.

A "stable" activation in contrast to a "transient" activation means that the immune cells maintain their phenotype, and in particular CCR6 and/or BLR1 expression over an extended period of time, as has been recently demonstrated by the present inventors for the Treg-specific transcription factor FOXP3 (Huehn J, Polansky J K, Hamann A. Epigenetic control of FOXP3 expression: the key to a stable regulatory T-cell lineage? Nat Rev Immunol. 2009; 9:83-89).

The method according to the present can be performed in vitro and/or in vivo. Preferred is a method according to the invention, wherein a demethylation, when compared to a non-activated T cell is indicative for a cell selected from stably activated T cells, NK cells, memory T cells, in particular CD4$^+$ or CD8$^+$ memory T cells, memory cytotoxic T cells, naïve B cells and memory B cells.

Further preferred is a method according to the invention, wherein said BLR1 and/or CCR6 positive immune cells, preferably NK cells, memory T cells, memory cytotoxic T-cells, naïve B cells, or memory B cells are stable BLR1 and/or CCR6 positive immune cells, preferably stable NK cells, memory T cells, in particular CD4$^+$ or CD8$^+$ memory T cells, memory cytotoxic T cells, naïve B cells and memory B cells, and CD25$^{high}$CD4$^+$ regulatory T-cells. The analysis of the accessibility of the BLR1 and/or CCR6 locus provides additional information, besides the mere expression of BLR1 and/or CCR6, to what extent a conversion into, for example, memory T cells lineage has occurred.

Even further preferred is a method according to the invention, wherein a demethylation in the gene ccr6 is indicative for a cell selected from CCR6$^+$ CD4$^+$ or CCR6$^+$ CD8$^+$ T cells, in particular of stably activated CCR6$^+$ CD4$^+$ or CCR6$^+$ CD8$^+$ T cells, and wherein said method optionally further comprises the step of isolating CD3$^+$ cells.

Whether stable CCR6 or BLR1 expression on human T cells is controlled by epigenetic mechanisms has not been studied so far. In general, the transcriptional regulation of CCR6 is not well understood; a region with promoter activity has been identified in the mouse CCR6 gene (Kucharzik T, Hudson J T, 3rd, Waikel R L, Martin W D, Williams I R. CCR6 expression distinguishes mouse myeloid and lymphoid dendritic cell subsets: demonstration using a CCR6 EGFP knock-in mouse. Eur J Immunol. 2002; 32:104-112), and over-expression of the transcription factor RORγt, the master regulator of Th17 cells, leads to CCR6 expression on human and murine T cells (Hirota K, Yoshitomi H, Hashimoto M, et al. Preferential recruitment of CCR6-expressing Th17 cells to inflamed joints via CCL20 in rheumatoid arthritis and its animal model. J Exp Med. 2007; 204:2803-2812. Manel N, Unutmaz D, Littman D R. The differentiation of human T(H)-17 cells requires transforming growth factorbeta and induction of the nuclear receptor ROR-gamma-t. Nat Immunol. 2008; 9:641-649). The inventors therefore investigated whether epigenetic mechanisms including DNA methylation of the CCR6 locus contribute to the regulation of stable CCR6 expression in human T cells. The inventors could identify a non-coding region in the CCR6 gene, harbouring transcriptional activity in primary T cells and being differentially methylated in human CCR6- and CCR6$^+$ T cells. These observations and the inducing effect of the DNA-methylation inhibitor 5'-azacytidine suggests that epigenetic mechanisms are involved in the regulation of stable CCR6 expression and the imprinting of distinct homing properties in human immune cells, in particular CCR6 positive memory T cells. Since a cell population reported to be involved in rheumatoid arthritis, the IL17 positive fraction has been shown to be CCR6 positive, this marker is of particular diagnostic value (see below). Preferred are applications where a fully quantitative methylation assay measuring the demethylation of this marker is performed.

Preferably, said analysis of the methylation status comprises analysing the methylation status of at least one CpG position in the 5' region upstream from the transcription start, promoter regions, introns, and/or exon/intron borders of the gene CCR6 and/or BLR1 or an orthologous or paralogous gene thereof, and in particular in the region overlapping the promoter region of the gene CCR6 according to SEQ ID NO 13 or an orthologous or paralogous region thereof.

The inventors have identified particulars region within the gene CCR6 and/or BLR1, which are functionally involved in the regulation of CCR6 and/or BLR1expression in immune cells. This region contains many CpG motifs, which display a differential methylation status when cells expressing BLR1, preferably memory T cells, naïve B cells, or memory B cells and/or CCR6, preferably NK cells, memory T cells, memory cytotoxic T-cells, naïve B cells, or memory B cells, compared with cells not expressing CCR6 and/or BLR1, if, for example, the bisulphite sequencing method is used. The inventors could demonstrate that in CCR6⁻ and BLR1⁻ cells the CpG motifs of the gene CCR6 and/or BLR1 are almost completely methylated (i.e. to more than 70%, preferably 80%, preferably, more than 90% and most preferred more than 95%), respectively, whereas the same motifs are completely demethylated in, for example, CCR6+ T-cells.

The differential methylation of the CpG motifs within the aforementioned region strongly correlates with CCR6 and/or BLR1 expression. Thus, determination of the methylation status of the CCR6 and/or BLR1 locus is a valuable tool to identify stable populations of selective immune cells required for clinical application in the treatment of rheumatoid arthritis, autoimmune disease, transplant rejection or allergy.

CCR6 has been described as a marker for activated immune cells, as its gene expression is observed in said cells, both when analysis is performed with mRNA transcripts and with antibodies against the protein. Those means of identification, however, solely recognize currently (and thus also transiently) activated cells. The assay systems are not capable of distinguishing stably activated T cells from those that only receive a stimulus but loose the functional phenotype shortly after this trigger has been given. The first group constitutes those lymphocytes that permanently express CCR6, and hence constitute the activated compartment. Only an analysis of the methylation pattern of lymphocytes allows the distinction between the two classes/subgroups, since only the stable CCR6 expressing, mid/long term activated lymphocytes are demethylated. Hence, in effect only methylation analysis identifies stable CCR6+ cells that constitute the true immune response and function exhibited by CCR6+ activated lymphocytes.

For a positive identification of activated T-lymphocytes, a pre-isolation (e.g. purification using, for example, cell sorting) of CD3 positive cells may be necessary, since for this scenario all B-cells are permanently CCR6+ and thus constitute a background "noise". However, within the T-lymphocyte compartment, only demethylated CCR6 cells can be considered fully and stably activated. While in cell culture permanently activated CCR6+ cells may be identified (using FACS MACS and mRNA) in isolated cultured form, this can not be achieved in a blood sample or a T cell-containing fraction thereof, since the measurement one identifies CCR6 positive (and BLR1+) cells at a single time point, and thus both stably activated and transiently activated cells. No marker for a distinction in blood is currently known. Surprisingly, the present methylation markers can achieve a distinction since transient CCR6/BLR1 protein producing cells remain methylated, whereas the permanently (stable) CCR6 positive/BLR1 positive counterparts are demethylated.

Preferred is a method according to the present invention, wherein said methylation status of at least one CpG position in the gene CCR6 and/or BLR1 or an orthologous or paralogous gene thereof is selected from an increased methylation for the gene BLR1 or an orthologous or paralogous gene thereof in granulocytes, monocytes, NK-cells, naïve T-cells, naïve cytotoxic T-cells, and memory cytotoxic T-cells, when compared to a respective CpG position in memory T-cells, naïve B-cells and/or memory B-cells, and an increased methylation for the gene CCR6 or an orthologous or paralogous gene thereof in granulocytes, monocytes, naïve T-cells, and naïve cytotoxic T-cells when compared to a respective CpG position in NK-cells, memory T-cells, memory cytotoxic T-cells, naïve B-cells and/or memory B-cells.

In the context of the present invention, the term "gene" shall mean a region of the chromosomal DNA that encodes for a certain protein, such as CCR6 and BLR1, and contains other genetic elements that are responsible for the regulation of said gene, such as, for example, the region overlapping the promoter region of the gene CCR6 according to SEQ ID NO 13 or an orthologous or paralogous region thereof. Thus, a gene includes also introns, enhancers, promoter sequences and the 5' untranslated region of the gene. In the present case, the gene will not only include the sequence as given in the accession numbers as indicated herein, but also includes the untranslated regions upstream and downstream thereof.

Some analyses as performed for the present invention have been performed in the murine system. Nevertheless, the regions that show differential methylation of CpG motifs between BLR1⁻ and BLR1⁺ and/or CCR6⁻ and CCR6⁺ cells are highly conserved among mammals, in particular between mice and human. In addition, experiments show that in the human system the same and/or homologous CpG motifs are demethylated as in murine BLR1⁺ and/or CCR6⁻ cells. In the context of the present invention, this fact is described by the terms "orthologous" or "paralogous" gene. An "ortholog" is a gene in two or more species that has evolved from a common ancestor, and is also called an orthologous gene. In the context of the present invention, Homo sapiens CCR6 is therefore an ortholog of the Mus musculus CCR6 gene and/or protein. "Paralogs" are genes related by duplication within a genome and are also called a paralogous gene. Orthologs retain the same function in the course of evolution, whereas paralogs evolve new functions, even if these are related to the original one. Included in the term "paralog" is a "pseudogene" that is a nucleotide sequences that is similar to a normal gene, but does not produce a functional final product. There are two variants of pseudogenes. The first requires the final product to be a protein. The second allows the final product to be an RNA.

Based on the information as given herein, the person of skill will be readily able, to compare the orthologous or paralogous genes (for example using a computer program in order to align the sequences, such as the ClustalW program), and to identify regions and/or CpG positions that can be found in the same regions and/or even at the same equivalent positions in the (both) genes. According to the present invention, these regions and/or CpG positions are regarded as orthologous or paralogous. Usually, an alignment is based on the level of sequence identity between the two (or more) DNA fragments that are analyzed. Levels of sequence identity are preferably about 75%, more preferably about 80%, and most preferred about 90% of a given fragment.

In order to analyze the methylation status of CpG positions, any known method to analyse DNA methylation can be used. In a preferred embodiment of the method according to the present invention, the analysis of the methylation status comprises a method selected from methylation specific enzymatic digests, bisulphite sequencing, analysis selected from promoter methylation, CpG island methylation, MSP, HEAVYMETHYL™, MethyLight, Ms-SNuPE or other methods relying on a detection of amplified DNA. These methods are well known to the person of skill, and can be found in the respective literature. Furthermore, also pooled samples can be used (e.g. of 5 samples or more), usually, a pool of samples is analyzed for the methylation status of at least one CpG position.

In a preferred embodiment of the method according to the present invention, said analysis of the methylation status for the gene CCR6 comprises amplification with at least one of the primer pairs selected from SEQ ID No. 1 and 2 ("amplicon 888"); SEQ ID No. 3 and 4 ("amplicon 1201"); SEQ ID No. 5 and 6 ("amplicon 1202"); SEQ ID No. 7 and 8 ("amplicon 1203"), and SEQ ID No. 11 and 12 ("DMR"), and orthologous or paralogous primer pairs thereof, and preferably said analysis of the methylation status comprises amplification with at least one of the primer pairs selected from SEQ ID No. 5 and 6; SEQ ID No. 7 and 8; SEQ ID No. 11 and 12; and orthologous or paralogous primer pairs thereof.

In another preferred embodiment of the method according to the present invention, said analysis of the methylation status for the gene BLR1 comprises amplification with at least one of the primer pairs selected from SEQ ID No. 9 and 10 ("amplicon 1037"-SEQ ID No. 29) and orthologous or paralogous primer pairs thereof.

Preferably, the amplification involves a polymerase enzyme, a PCR or chemical amplification reaction, or other amplification methods as known to the person of skill and as described below, e.g. in the context of MSP, HEAVYMETHYL™, or MethyLight. In another aspect of the present invention, oligomers according to any of SEQ ID No. 1 to 12 or an amplicon (e.g. according to SEQ ID No. 13) as amplified by a primer pair selected from SEQ ID No. 1 and 2, SEQ ID No. 3 and 4, SEQ ID No. 5 and 6, and SEQ ID No. 7 and 8, and SEQ ID No. 9 and 10, and SEQ ID No. 11 and 12 or orthologous or paralogous oligomers or amplicons constitute preferred embodiments of the present invention.

Based on the above information and the data as obtained from the murine system, orthologous or paralogous primer pairs can be designed by the person of skill having a sequence identity with the above primers of preferably about 75%, more preferably about 80%, and most preferred about 90%. Particularly preferred is a method according to the present invention, wherein said analysis of the methylation status comprises amplification with at least one of the primer pairs selected from SEQ ID No. 5 and 6; SEQ ID No. 7 and 8; SEQ ID No. 11 and 12; and orthologous or paralogous primer pairs thereof.

Further preferred is a method according to the present invention, wherein the analysis of the methylation status comprises analysing the methylation status of at least one CpG position selected from the group consisting of nucleotide positions 71, 98, 106, 135 178, 193, 277, 316, and 339 of the amplicon as amplified by the primer pair SEQ ID No. 1 and 2, positions 23, 36, 38, 53, and 114 of the amplicon as amplified by the primer pair SEQ ID No. 3 and 4, positions 23, 109, 161, 193, 217, and 245 of the amplicon as amplified by the primer pair SEQ ID No. 5 and 6, positions 62, 101, 124, 202, 246, and 251 of the amplicon as amplified by the primer pair SEQ ID No. 7 and 8, positions 71, 98, 106, 135, 178, 193, 277, and 316 of the amplicon as amplified by the primer pair SEQ ID No. 11 and 12, and orthologous or paralogous CpG positions thereof.

Further preferred is a method according to the present invention, wherein the analysis of the methylation status comprises analysing the methylation status of at least one CpG position selected from the group consisting of positions 23, 25, 46, 51, 109, 157, 177, 183, 199, 229, 244, 247, 287, and 360 of the amplicon as amplified by the primer pair SEQ ID No. 9 and 10, and orthologous or paralogous CpG positions thereof. It could be shown in the experiments that these positions were mostly demethylated in the activated T cells. The person of skill will furthermore be able to select specific subsets of CpG positions in order to minimise the amount of sites to be analyzed, for example all sites as present on amplicon 888 and/or all sites as present on amplicon 1037, or the DMR, or orthologous or paralogous CpG positions thereof.

The method according to the present invention can be performed with any mammal having the gene BLR1 and/or CCR6 or an ortholog or paralog thereof, preferred is a method according to the present invention, wherein said mammal is a mouse, rat, monkey or human.

In another aspect of the present invention, the present invention provides a method for diagnosing the immune status of a mammal, comprising the steps of a) obtaining a sample containing immune cells from said mammal to be diagnosed, b) analysing the methylation status of at least one CpG position in the gene CCR6 and/or BLR1 or an orthologous or paralogous gene thereof according to the present invention in said immune cells, c) identifying the amount and/or type of immune cells present in said sample based on said methylation status, and d) concluding on the immune status of said mammal based on said amount and/or type as identified.

In one aspect of this method, the overall population of T cells in a sample (containing different types of immune cells) is analyzed for their methylation status in the CCR6 and/or BLR1 gene. Based on the result of the overall methylation frequency of the sites, the ratio and/or amount of, for example, memory T cells inside the analyzed population can be determined. From said result, it can be concluded on the immune status and/or T cell status of the mammal as diagnosed. The method can be performed in vitro and/or in vivo. In general, all biological samples can be used, as long as they contain suitable T-cells. Preferred is a method, wherein said sample is selected from a blood sample, a sample of blood lymphocytes or a fraction thereof. Most preferred, a sample comprises T cells purified via CD3, preferably using cell sorting or magnetic beads (MACS). This method can also be used to produce B cell containing samples for analysis.

The method according to the present invention can be performed with any mammal having the gene ccr6 and/or blr1 or an ortholog or paralog thereof, preferred is a method according to the present invention, wherein said mammal is a mouse, rat, monkey or human. Preferred is a method, wherein said mammal is a patient suffering from a disease selected from autoimmune diseases, adverse effects in autoimmune diseases, adverse effects in allotransplantate recipients, tumorous diseases, ovarian cancer, chronic graft-versus-host disease, allergic asthma, multiple sclerosis, inflammations, inflamed joints, rheumatoid arthritis, psoriatic disease, inflammatory bowel disease, encephalopathy, and immunodysregulation polyendocrinopathy enteropathy X-linked syndrome (IPEX). Preferably, said disease is rheumatoid arthritis. These diseases and their relations to immune cells have been described in the respective literature.

Further preferred is a method, wherein the amount of BLR1+ and/or BLR6+ immune cells, preferably activated T cells, NK cells, memory T cells, memory cytotoxic T-cells, naïve B cells, or memory B cells, corresponds to a demethylation of the CpG positions as analyzed to at least 80%, preferably 90%, and more preferably 95%. Even further preferred is a method that further comprises measuring and/or monitoring the amount and/or or ratio of said immune cells in response to chemical and/or biological substances that modulate CCR6 and/or BLR1 expression in the immune cell. That is, changes in the amount or ratio of immune cells that are caused by, for example, the treatment of a disease (e.g. as described herein), and the success and/or progress of said treatment in terms of an effect on immune cells can be followed using this method. A follow-up of the methylation pattern of immune based on the marker herein will point to changes in the cells that are due to a response to said chemical and/or biological substances, in some cases even before a phenotypic change can be observed. This information can be then used for adjusting therapies against the underlying or related diseases (as, for example, mentioned herein), and thus allow for an improved and more effective treatment and/or prevention, which includes avoiding and/or reducing sideeffects.

In yet another aspect of the present invention, the present invention provides a method for determining the suitability of in vitro generated or expanded immune cells for a transfer into a patient, comprising the method according to the invention, and detecting, whether the CpG positions as analyzed are methylated to at least 80%, preferably 90%, and more preferably 95%. The method can be performed in vitro and/or in vivo. For example, immune cells that appear to show a modified, in particular a drop, of CCR6 and/or BLR1 expression are usually not regarded as stable and will not be used further.

In yet another aspect of the present invention, the present invention provides a method for identifying chemical and/or biological substances that modulate the CCR6 and/or BLR1 expression in an immune cell, comprising contacting one or more of said chemical and/or biological substances with an immune cell, performing the method according to the present invention as described herein, and detecting, whether said chemical and/or biological substance modulates methylation of the CpG positions as analyzed. The method can be performed in vitro and/or in vivo. In this aspect, the present invention encompasses a method, sometimes called a "screening-method", that seeks to identify chemical and/or biological substances modulating CCR6 and/or BLR1 expression that can be used as starting points for the development of regulatory T cell specific medication and respective pharmaceutical compositions. The present method is based on the fact that it is well accepted that the CCR6 and/or BLR1 gene play a central role for the development of the immune cells as described herein, such as NK cells, memory T cells, memory cytotoxic T-cells, naïve B cells, or memory B cells. Therefore, factors modulating CCR6 and/or BLR1 expression are also interesting tools to treat autoimmune diseases or allotransplantate recipients. Even factors preventing CCR6 and/or BLR1 expression are interesting for the treatment of tumour patients, where BLR1+ and/or CCR6+ immune cells, preferably NK cells, memory T cells, memory cytotoxic T-cells, naïve B cells, or memory B cells have been shown to prevent a strong anti tumour response.

Such factors that lead to a stable modification of CCR6 and/or BLR1 expression, can be detected with the method described in this invention. Furthermore, factors that can enhance the differentiation of immune cells and lead to an alleviation of autoimmune and allergenic disorders can be identified with the present method. Chemical and/or biological substances that are suitable as screening compounds are known to the person of skill and, for example, include small molecules, peptides and proteins, and antibodies or fragments thereof. Furthermore, the screening can be done using a commercially compound library, optimally together with suitable automation, such as a robot. In one preferred embodiment of the method for identifying chemical and/or biological substances, said substance provides a demethylation of the CpG positions as analyzed to at least 80%, preferably 90%, and more preferably 95%.

Another preferred method according to the present invention is a method for the diagnosis of diseases that are associated with the aberrant expression of the gene CCR6 and/or BLR1, comprising the method according to the present invention as described herein, and detecting, whether the CpG positions as analyzed are demethylated to at least 80%, preferably 90%, and more preferably 95%, wherein the diseases are selected from autoimmune diseases, adverse effects in allotransplantate recipients, tumorous diseases, ovarian cancer, chronic graft-versus-host disease, allergic asthma, and IPEX syndrome. The present method can be performed in vitro and/or in vivo.

Another preferred aspect of the present invention relates to a kit for identifying immune cells, such as activated T cells, preferably naïve T cells or memory T cells, based on the analysis of the methylation status of CpG positions in the gene CCR6 and/or BLR1, comprising materials for performing a method according to the present invention. In one preferred embodiment according to the present invention, the kit comprises a) a bisulfite reagent, and b) materials for the methylation analysis of CpG positions as given above. The person of skill will furthermore be able to select materials for specific subsets of CpG positions in order to minimise the amount of sites to be analyzed, for example all sites as present on amplicon 888 and/or all sites as present on amplicon 1037 and/or all sites as present on the amplicon according to SEQ ID No. 13 (DMR), or orthologous or paralogous CpG positions thereof. The kit can be a diagnostic kit.

The kits according to the present invention may preferably also contain: 1. Chemicals (bisulfite, etc.) for processing the cell samples; 2. Procedure protocols; 3. Oligonucleotide probes, amplicons, blockers or extension primers according to the present invention that will detect markers relevant to a particular cell type. The oligonucleotides would be constructed to generate a signal on a commonly available detection platform, such as Real Time-PCR (RTPCR) or Single Base Extension (SBE). Each signal indicates the level of methylation at a particular target site in the sample. As an alternative, probes according to the described nucleic acids could be produced for usage on a chip; 4. A bioinformatic tool to process the results. This, e.g., software might normalise the signals from the raw data, contain a result matrix for interpretation of the read-out, or implement various algorithms that calculate, for example, cell type proportions, or potency predictions.

Yet another preferred aspect of the present invention relates to the use of an oligomer or amplicon according to the present invention or a kit according to the present invention for detecting and/or identifying immune cells, preferably naïve T cells or memory T cells, in analogy to what has been described above.

Yet another preferred aspect of the present invention relates to a method of treatment of diseases that are related to CCR6 and/or BLR1 expression, autoimmune diseases, adverse effects in allotransplantate recipients, tumorous diseases, ovarian cancer, chronic graft-versus-host disease, allergic asthma, multiple sclerosis, inflammations, inflamed joints, rheumatoid arthritis, psoriatic disease, inflammatory bowel disease, encephalopathy, and immunodysregulation polyendocrinopathy enteropathy X-linked syndrome (IPEX), preferably rheumatoid arthritis, psoriatic disease, inflammatory bowel disease, most preferred rheumatoid arthritis. The method comprises administering an effective amount of immune cells as characterized according to the present invention using CCR6 and/or BLR1 expression to said patient in need thereof. How to administer effective amounts of immune cells, is described in the literature (for example in Bharat A, Fields R C, Mohanakumar T. Regulatory T cell-mediated transplantation tolerance. Immunol Res. 2006; 33(3):195-212. June C H, Blazar B R. Clinical application of expanded CD4(+)25(+) cells. Semin Immunol. 2006 Jan. 31; Khazaie K, von Boehmer H. The impact of CD4(+)CD25(+) Treg on tumor specific CD8(+) T cell cytotoxicity and cancer. Semin Cancer Biol. 2006 April; 16(2):124-136. Epub 2006 Jan. 26., and the references as cited therein), and the person of skill will be able to apply these methods in the context of the present invention. The term "treatment" also includes a prevention of said CCR6 and/or BLR1 expression related diseases.

The analysis of the methylation status of the region within the CCR6 and/or BLR1 loci allows an improved prediction whether the cell population will stably express the CCR6 and/or BLR1 gene or not. Therefore, this method can be used as a quality control for in vitro generated or expanded immune cells before adoptive transfer into patients which suffer from autoimmune diseases or which have received an allotransplant. Only if the CpG motifs are demethylated to a certain degree it is confident that these cells will stably express the CCR6 and/or BLR1 gene and will not loose CCR6 and/or BLR1 expression after some period of time. Such a "quality control" concerning the stability of the regulatory phenotype of adoptively transferred cells is absolutely required and can be achieved only by the analysis of the methylation status of the aforementioned region(s) of the CCR6 and/or BLR1 loci.

In one embodiment of the present invention and as described herein, the methylation status of the CCR6 and/or BLR1 locus was analyzed by bisulphite sequencing and revealed striking differences between granulocytes, monocytes, naïve T-cells or naïve cytotoxic T-cells and NK cells, memory T cells, memory cytotoxic cells, naïve B cells, or memory B cells. For CCR6, amplicon 888 and amplicon 1203 (see examples) displayed a high degree of methylation (nearly 100%) within conventional granulocytes, monocytes, naïve T-cells or naïve cytotoxic T-cells (FIGS. 8A, 8B, and 9). Amplicon 1204 (SEQ ID No. 26; see examples) showed a high degree of methylation (nearly 100%) within conventional naïve T-cells and naïve cytotoxic T-cells. In amplicons 1201 and 1202 (see examples), demethylation process occurs only in naïve B cells and memory B cells, showing that demethylation is not a random event, but confined to defined regions. In particular, a region was identified in the CCR6 locus (see SEQ ID No. 13), which displayed a high degree of demethylation (nearly 100%) within CCR6$^+$ CD4$^+$ and CD8$^+$ memory T cells.

As with the BLR1 locus, amplicon 1037 (see examples) displayed a high degree of methylation (nearly 100%) within conventional granulocytes, monocytes, NK cells, naïve T-cells, memory cytotoxic T cells or naïve cytotoxic T-cells (FIG. 8).

Differential expression of distinct chemokine receptors on immune cells ensures a coordinated temporal-spatial distribution of various functional subsets and differentiation stages of effector and regulatory cells to and within lymphoid and non-lymphoid tissues. Some of the migratory phenotypes, especially of T and B cells, become apparently permanently imprinted upon differentiation and allow a selective delivery of memory populations to specific compartments of the body ("homing"). How stable homing phenotypes are acquired and maintained in the progeny of T and B cells is not well understood. Epigenetic mechanisms, notably the methylation/demethylation of DNA regions as described herein involved in transcriptional regulation, are ideally suited to provide a long-term memory of phenotypic changes due to the imprinting of "heritable" methylation signatures. In the context of the present invention, the inventors thus investigated whether differential DNA methylation might be involved in the acquisition of stable CCR6 expression in primary human T cells.

In the context of the present invention, surprisingly a region (SEQ ID No. 13, DMR) within the CCR6 locus being differentially methylated among subpopulations of leukocytes was initially identified by a DMH approach (Baron U, Floess S, Wieczorek G, et al. DNA demethylation in the human FOXP3 locus discriminates regulatory T cells from activated FOXP3+ conventional T cells. Eur J Immunol. 2007; 37:2378-2389.) and was verified by analyzing the methylation status of sorted human blood cell subsets using bisulfite conversion. The observed methylation pattern matches largely the expression of CCR6 in various lymphocyte subsets, where CCR6-expressing cells such as CD56$^+$ NK and NKT cells, some CD4$^+$ and CD8$^+$ T cells, mature B cells and CD4$^+$ Tregs displayed a partially or even completely demethylated CCR6 region, whereas the locus was completely methylated in resting CD14$^+$ monocytes and CD15$^+$ granulocytes lacking CCR6 expression.

Nevertheless, among CD4$^+$ and CD8$^+$ memory T cells, demethylation of the CCR6 region is confined to those subsets expressing the CCR6 protein on their surface, suggesting a role for this genetic element and its methylation status in CCR6 regulation.

Demethylation of DNA is usually seen as a signature for a stable, heritable expression pattern, as the inventors could recently demonstrate for the Treg-specific transcription factor FOXP3 (Huehn J, Polansky J K, Hamann A. Epigenetic control of FOXP3 expression: the key to a stable regulatory T-cell lineage? Nat Rev Immunol. 2009; 9:83-89).

Like many other receptors for inflammatory chemokines, CCR6 is expressed on a large portion of circulating memory T cells, but absent from naive T cells (Liao F, Rabin R L, Smith C S, Sharma G, Nutman T B, Farber J M. CC-chemokine receptor 6 is expressed on diverse memory subsets of T cells and determines responsiveness to macrophage inflammatory protein 3 alpha. J Immunol. 1999; 162:186-194; Sato K, Kawasaki H, Nagayama H, et al. Chemokine receptor expressions and responsiveness of cord blood T cells. J Immunol. 2001; 166:1659-1666), suggesting that CCR6 expression is acquired during T cell priming. CCR6 expression can be induced de novo from naive CCR6$^-$CD4$^+$ T cells using a cytokine cocktail containing IL-1, IL-6, TGF-β and TNF-α (Acosta-Rodriguez E V, Rivino L, Geginat J, et al. Surface phenotype and antigenic specificity of human interleukin 17-producing T helper memory cells. Nat Immunol. 2007; 8:639-646; Sato K, Kawasaki H, Nagayama H, et al. Chemokine receptor expressions and responsiveness of cord blood T cells. J Immunol. 2001; 166:1659-1666).

Even though the percentage of CCR6$^+$ cells is increased with repetitive stimulations under inducing conditions, the achieved CCR6 expression was neither found to be stable upon prolonged culture, contrasting to CCR6$^+$ ex vivo sorted memory T cells, nor was it associated with a demethylation of the CCR6 region, which proved to be characteristic for the CCR6$^+$ memory population. The methylation status in memory cells might be independent from the functional phenotype, as the inventors see demethylation of the CCR6 region in IL-17-secreting and non-secreting CCR6$^+$ cells. Together, the data as provided by the present invention suggests that specific, so far unknown signals are required to imprint a stable CCR6 expression profile in CD4$^+$ T cells.

Finally, a lack of correlation between DNA methylation and the actual expression of CCR6 was found for the down-regulation of CCR6 on CD4$^+$ memory T cells following TCR-stimulation: the transient loss of CCR6 expression was not accompanied by a change in the methylation pattern. Here again, the change in expression was not stable as CCR6 was rapidly re-expressed after removal of the TCR-stimulus and addition of IL-2. For this case, however, it cannot be excluded that CCR6 down-regulation was due to receptor modulation rather then transcriptional regulation of CCR6 expression. These data show that DNA methylation in a critical region of the CCR6 locus is involved in the acquisition of a permanently CCR6-expressing phenotype in memory T cells.

The result that the methylation status of regulatory gene elements in the CCR6 locus dictates long-term stability of CCR6 expression was further corroborated by experiments involving artificial DNA hypomethylation. Application of the DNA methyltransferase inhibitor 5'-azacytidine during T cell stimulation not only increased CCR6 expression, even in absence of exogenous CCR6-inducing cytokines, but also resulted in CCR6$^+$ cells that showed stable CCR6 expression upon in vitro expansion, a finding that was previously also observed for Foxp3 expression in in vitro induced Tregs (Polansky J K, Kretschmer K, Freyer J, et al. DNA methylation controls Foxp3 gene expression. Eur J Immunol. 2008; 38:1654-1663).

Here, the inventors identified and characterized a non-coding region of the human CCR6 locus, displaying unmethylated CpG motifs in CCR6-expressing memory CD4$^+$ and CD8$^+$ T cells and CD25$^{high}$FOXP3$^+$ Tregs. CCR6 expression on CCR6$^+$ memory CD4$^+$ T cells was stable upon cytokine-induced proliferation and slightly down-regulated upon TCR stimulation. However, such CCR6 down-regulation was only transient and not accompanied by remethylation of the regulatory region within the CCR6 locus. Conversely, in vitro induction of CCR6 expression in naive CD4$^+$ T cells upon TCR stimulation in the presence of inflammatory cytokines resulted in unstable CCR6 expression and displayed no change in the methylation status of the CCR6 locus. Notably, treatment with the DNA methylation inhibitor 5'-azacytidine led to increased and partially stable CCR6 expression. When cloned into a reporter gene plasmid this differentially methylated region displayed constitutive transcriptional activity upon transfection into ex vivo isolated CCR6$^+$ primary T cells, demonstrating that it might act as an enhancer element to regulate CCR6 expression.

In summary, the inventors have identified a non-coding region of the human CCR6 gene showing constitutive transcriptional activity in CCR6$^+$ T cells that mediates stable CCR6 expression via epigenetic mechanisms. The present invention provides for the first time experimental evidence that epigenetic mechanisms are not only regulating the transcriptional activity of a chemokine receptor but moreover might play a key role in the imprinting of a permanent expression pattern, thus endowing differentiated memory T cells with topographical memory and shaping their long-term migratory behavior.

BRIEF DESCRIPTION OF THE FIGURES

The file of this patent contains at least one drawing executed in color. Copies of this patent with color drawings(s) will be provided by the Patent and Trademark Office upon request and payment of the necessary fee.

The present invention shall now be further described in the following examples with reference to the accompanying figures and sequence listing, nevertheless, without being limited thereto. In the Figures.

FIG. 3 shows that CCR6$^+$ T cells stably express CCR6 upon in vitro expansion and maintain a demethylated CCR6 region. A) CFSE-labeled CCR6$^+$CD4$^+$ memory T cells were cultured for six days in medium containing recombinant human IL-7 and IL-15 (both 10 ng/ml) or anti-CD3/anti-CD28 Dynabeads® with and without TGF-β and reanalyzed for CCR6 expression. One representative donor out of four is shown. B) CCR6$^+$CD4$^+$ memory T cells were stimulated with anti-CD3/anti-CD28 Dynabeads® under neutral conditions or with TGF-13 (10 ng/ml). After six days, CCR6 expression was reanalyzed. Grey shaded cusrves display the isotype control. C) Methylation analysis of the CCR6 region was assessed for CCR6$^+$ cells cultured for six days as in B for two donors. D) CCR6$^+$ cells were stimulated with anti-CD3/anti-CD28 Dynabeads® under neutral conditions, sorted on day 6 in CCR6$^-$ and CCR6$^+$ cells and cultured for additional three days in medium containing IL-2 (1000 U/ml). Data are representative for two donors.

FIG. 6 shows that the preferred differentially methylated CCR6 region encompasses transcriptional activity. Total CD4+ T cells were transfected with pGL3-Promoter plasmid, containing the SV40 minimal promoter in front of the luciferase reporter gene, or pGL3-CCR6, where the CCR6 region was cloned in front of the SV40 promoter. After nucleofection, cells were cultivated in medium containing IL-2 (white bars) or stimulated with PMA and Ionomycin for four hours (grey bars). The relative luciferase light units were normalized to Renilla luciferase activity. Values for the pGL3-Promoter plasmid were set to 1 to obtain the x-fold activation. Bars show the mean luciferase activity of cells from five different donors, the lines display the distribution area of the single values.

FIG. 7 shows the human CCR6 demethylated region (DMR) on chromosome 6, together with the factor-binding sites as predicted.

FIG. 9 shows the methylation analysis of the CCR6 locus at various different positions of the CCR6 gene. This comparison includes various leukocyte cell types other than cytotoxic and helper T cells. The data show that in Amp 1201 demethylation only is observed in memory and naïve B cells, while all other leukocyte fractions including CD15+ granulocytes, CD14+ monocytes CD56+ Nk cells, and all T cell fractions are fully methylated. In the amplicon 888, in addition to the memory fractions of both CD4 and CD8 T cells, NK cells, and B cell are demethylated.

Figure 1:
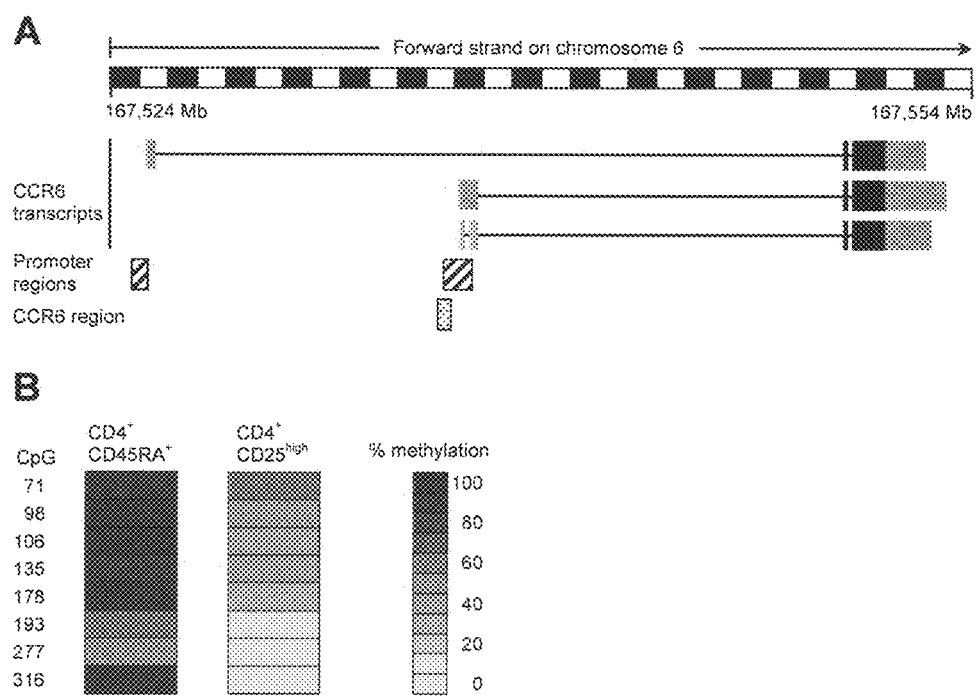
FIG. 1 shows that the preferred non-coding region in the CCR6 gene displays differential methylation in human PBMCs. A) Localization of the CpG-rich region within the human CCR6 locus. The exon structure of the putative CCR6 transcripts, obtained from the Ensembl database (GRCh37), were plotted together with the predicted promoter regions (Genomatix) and the identified differentially methylated region in the CCR6 locus. The gray shaded boxes in the CCR6 transcripts represent non-coding exon regions, whereas the black boxes contain coding regions. B) DNA methylation pattern for CCR6 were analyzed from pooled PBMC (five donors) and sorted into CD4$^+$CD45RA$^+$ and CD4$^+$CD25$^{high}$. Each column represents one blood cell subset with each row representing a single CpG site. DNA methylation was measured by means of bisulfite sequencing. CpG methylation levels are color coded according to the color scale ranging from light gray (0% methylation) to dark gray (100% methylation).

Seq IDs No 1 to 12, and 14 to 28 show primers and probes as used in the examples.

Seq ID No 13 shows the region overlapping the promoter region of the gene ccr6 according to the invention.

Seq ID No 29 shows the sequence of amplicon 1037.

EXAMPLES

Although the following examples were mainly performed in the context of an analysis of a preferred demethylated region of the gene CCR6, the person of skill will realize that these experiments can be readily adjusted for a methylation analysis of other relevant regions of the gene as described herein for CCR6, and for BLR1.

Material and Methods

Cells, Antibodies and Flow Cytometry

Buffy coats (DRK Blutspendedienst, Berlin, Germany) and peripheral blood samples were obtained from healthy donors after informed consent in accordance with local ethical committee approval. PBMCs were separated with a Ficoll-Hypaque gradient (Sigma-Aldrich). Cell surface antigens were analyzed by single-parameter or multi-parameter fluorescence-activated cell sorter (FACS) analysis using the following monoclonal antibodies: PE-anti-CCR6 (11A9) and Alexa700-anti-CD4 (RPA-T4) (both from BD Biosciences). APC-anti-CD25 (BC96) was purchased from ebioscience. PE-Cy5-anti-CD8 (B9.11), PE-Cy5-anti-CD56 (N901) and FITC-anti-CD25 (B1.49.9) from Beckman Coulter. Antibodies generated in house (DRFZ, Berlin): FITC-anti-CD45RA (4G11), Alexa405-anti-CD4 (TT1) and Alexa405-anti-CD3 (OKT3). In some experiments, CCR6 expression was detected by indirect immunofluorescence using biotinylated CCR6 (11A9, BD Biosciences) followed by staining with APCconjugated streptavidin (SouthernBiotech). Stains were performed in Phosphate buffered saline containing 0.5% bovine serum albumin to block unspecific binding. A FACSCanto II (BD Biosciences) was used for data acquisition and analysis was performed using FlowJo software (Treestar).

T-Cell Isolation and FACS® Sorting

Total $CD4^+$ and $CD8^+$ T cells were enriched from PBMCs using anti-CD4 or anti-CD8 magnetic beads, respectively, and the autoMACS separation system according to the manufacturers instructions (Miltenyi Biotec, Bergisch Gladbach, Germany). After subsequent staining with anti-CD4, anti-CD8, anti-CD25, anti-CD45RA and anti-CCR6 the following cell populations were sorted on a FACSAria® or FACSDiva® cell sorter (BD Biosciences): naive $CD4^+$ T cells ($CD4^+CD25^-CD45RA^+$), $CD4^+$ Tregs ($CD4^+CD25^{high}$), $CCR6^-$ naive $CD4^+$ T cells, $CCR6^-$ memory $CD4^+$ T cells ($CD4^+CD25^-CD45RA^-$), $CCR6^+$ memory $CD4^+$ T cells, $CCR6^-$ naive $CD8^+$ T cells ($CD8^+CD25^-CD45RA^+$), $CCR6^-$ memory $CD8^+$ T cells ($CD8^+CD25^-CD45RA^-$) and $CCR8^+$ memory $CD8^+$ T cells. Upon re-analysis, sorted cells routinely showed >98% purity. Ex vivo isolated cells were either used for methylation analyses or for in vitro cell cultures (see below).

T-Cell Culture of Naive and Memory $CD4^+$ T Cells

For in vitro culture assays, cells were cultured in RPMI 1640 Glutamax medium (Invitrogen) containing 100 U/ml penicillin, 100 μg/ml streptomycin, 1 mM sodium pyruvate, non-essential stimulation, β-mercaptoethanol, and 5% human serum (complete medium [CM]). For stimulation of naive $CD4^+$ T cells, $1\times10^5$ cells were cultured in CM supplemented with 20 ng/ml IL-2 (R&D Systems) and 2 μg/ml neutralizing antibodies against IL-4, IL-12 and IFN-γ (neutral conditions, antibodies from BD Biosciences) in flat-bottom microtiter plates and $1\times10^5$ magnetic beads coated with anti-CD3 and anti-CD28 (Dynabeads, Invitrogen) for four days followed by transfer in CM containing 1000 U/ml IL-2 (Proleukin, Chiron). For induction of CCR6 on naive $CD4^+$ cells, the following cytokines were added at the beginning of the culture: 10 ng/ml TGF-β, 10 ng/ml IL-6, 10 ng/ml IL-1, 10 ng/ml TNF-α (R&D). In some experiments, stimulation of cells was repeated up to three times under the same conditions. For induction of CCR6 on naive $CD4^+$ cells with the methylation inhibiting drug 5' Azacytidine (Aza, Sigma-Aldrich) 5 μM Aza was added after 48 hours of culture.

Memory $CD4^+CCR6^+$ and $CD4^+CCR6^-$ cells were stained with carboxyfluorescein succinimidyl ester (CFSE) and cultured either in CM containing magnetic beads as described above or 10 ng/ml IL-7 and 10 ng/ml IL-15 (R&D Systems). After four days only the cultures containing Dynabeads were transferred in CM containing 1000 U/ml IL-2 (Proleukin, Chiron). At the end of the cultures, cells were analyzed by flow cytometry and used for methylation analyses (see below).

Luciferase Reporter Assay

The differentially methylated region of the human CCR6 locus was amplified by PCR using human cDNA as a template and the following primers: (A) 5'-GAC-TACGCGTCAGTAAGGGGGAGCCACTG-3' (SEQ ID NO 11), (B) 5'-GACTAGATCT CAAGGAAAGCAGCT-GACGA-3' (SEQ ID NO 12). The amplified 501 bp element was cloned via M/uI and BglII into the pGL3 promoter vector (Promega) in front of a minimal SV40 promoter to generate pGL3-CCR6. Sequencing of the cloned region revealed a 100% identity with the CCR6 region sequence of the homo sapiens genome stored at Ensembl.

MACS-sorted total $CD4^+$ T cells were transfected using 2.5 μg of pGL3 promoter vector or pGL3-CCR6 vector. Synthetic Renilla luciferase reporter vector (pRL-TK; Promega) (1.5 μg) was used as an internal control for transfection efficiency. 4 h after transfection via nucleofection (Lonza), cells were cultivated in RPMI 1640 medium containing IL-2 or prior stimulated for 4 h with PMA (10 ng/ml; Sigma) and Ionomycin (500 ng/ml; Sigma). After 48 h of culture, cells were harvested and luciferase activity was measured using the dual luciferase assay system (Promega). Data were normalized to Renilla luciferase activity.

Primers, DNA Preparation, Bisulfite Conversion, PCR and Sequencing

Primers were used for bisulfite-specific PCR and sequence reactions. Genomic DNA was isolated from sorted T cell subsets using the DNeasy tissue kit (Qiagen) following the protocol for cultured animal cells. Bisulfite treatment of genomic DNA was performed as previously described (Olek A, Oswald J, Walter J. A modified and improved method for bisulphite based cytosine methylation analysis. Nucleic Acids Res. 1996; 24:5064-5066.). PCR was performed in a final volume of 25 μL containing 1×PCR Buffer, 1 U Taq DNA polymerase (Qiagen), 200 μM dNTP, 12.5 pmol each of forward and reverse primers, and 7 ng bisulfite-treated genomic DNA at 95° C. for 15 min, and 40 cycles of 95° C. for 1 min, 55° C. for 45 s and 72° C. for 1 min, and a final extension step of 10 min at 72° C. PCR products were purified using ExoSAP-IT (USB Corp.) and sequenced applying the PCR primers and the ABI Big Dye Terminator v1.1-chemistry (Applied Biosystems) followed by capillary electrophoresis on an ABI 3100 genetic analyzer. AB1 files were interpreted using ESME (Lewin J, Schmitt A O, Adorjan P, Hildmann T, Piepenbrock C. Quantitative DNA methylation analysis based on four-dye trace data from direct sequencing of PCR amplificates. Bioinformatics. 2004; 20:3005-3012.).

Examples for preferred primers and probes are:

Amplification primer for amplicon 888 (for bisulfite sequencing):

```
Fw: (888p)
                                      (SEQ ID No. 1)
GTTAGTGGGGTTGAGTAGGATA

Rev: (888o)
                                      (SEQ ID No. 2)
AAAACCCTAAAATCACAAAACTA
```

Amplification primer for amplicon 1201 (for bisulfite sequencing):

1201q
(SEQ ID No. 3)
TTGGTAATGTTTGTTTGGAAAG 1201r
(SEQ ID No. 4)
CTCCTAAATCCCTCAACATCTA

Amplification primer for amplicon 1202 (for bisulfite sequencing):

1202o
(SEQ ID No. 5)
AAACTCACAACTTCCTTCACTC 1202p
(SEQ ID No. 6)
AAGGGTAGTGTTAGAGGGTATTT

Amplification primer for amplicon 1203 (for bisulfite sequencing):

1203o
(SEQ ID No. 7)
CACCTAATCTTCATATAACACAAAA 1203p
(SEQ ID No. 8)
GGTATAGTGTATTGGGAAGTGG

Amplification primer for amplicon 1204 (for bisulfite sequencing):

1204r
(SEQ ID No. 27)
TCTCTTTTTCTTATCACTTTACCA 1204q
(SEQ ID No. 28)
TGTTTTTAGGAAAGGAAGTTTG

Amplification primer for amplicon 1037 (SEQ ID No. 29; for bisulfite sequencing):

1037o
(SEQ ID No. 9)
CCTTATCTACTTCTTCCACAAAAT 1037p
(SEQ ID No. 10)
AGTGATGAGTTGTGAGGTAGGT

Amplification primer for DMR (for bisulfite sequencing):

CpG (Methyl)-specific PCR-system
Fw-Primer
(SEQ ID No. 14)
GAGATGATAAGGGGTGC

Rev-Primer
(SEQ ID No. 15)
ACACCTCACCTAAATCG

Probe
(SEQ ID No. 16)
HEX-TTTAGGCGTGAGGACGTGGAGTT-BHQ1

TpG (De-methyl)-specific PCR-system
Fw-Primer (SEQ ID No. 17)
GAGATGATAAGGGGTGT

Rev-Primer
(SEQ ID No. 18)
ACCACACCTCACCTAAATCA

Probe
(SEQ ID No. 19)
FAM-ATTTAGGTGTGAGGATGTGGAGTTTAGGG-BHQ1

Genomic Target region of the CCR6 DMR assay is indicated in bold, CpGs are underlined GCCAGTGGGGT-TGAGCAGGACACAGGTCCTGCTGTGTCTAGCTGGT-TCCCCAGAG AGATGATAAGGGGTG CGCTCCAGCTTCTCAGGCTCACTCAGGCGTGAGGA CGTGGAGCTCAGGGCTCTGCAGGAAGGAG CGACCCAGGTGAGGTGTGGTCAA GATAGAGCA-GAGCTGGGCAGCGGGCAGTGGAGCCT CGTGGGCAGCCTGGGGGTG GGGAGGCACAGTG-CACTGGGAAGTGGAGAAAGTGTGAGTCCATCAG-GCTGGCTG AGAATTGATCA CGAACCTATTGTCTGTAAAACTTTTGTTATTTCC TGAGACGTGGT TCACAGCAACCCAGGTG CGAACAGCCTTGTGATTCTAGGGTTCT (SEQ ID No. 13)

In Silico Analyses

For prediction of putative transcription factor binding sites the tool MatInspector (Genomatix) was used.

Statistics

Data are expressed as the mean±SD. Differences between groups were assessed using the Mann-Whitney test or Wilcoxon rank test as indicated. P values<0.05 were considered significant.

Example 1

A Non-Coding Region in the CCR6 Locus Displays Differential Methylation Correlating with CCR6 Expression The inventors had previously conducted a screen for epigenetically regulated genes in human Tregs by comparing conventional naive CD4$^+$ T cells and CD25$^{high}$CD4$^+$ Tregs using the differential methylation hybridization (DMH) technique (Baron U, Floess S, Wieczorek G, et al. DNA demethylation in the human FOXP3 locus discriminates regulatory T cells from activated FOXP3+ conventional T cells. Eur J Immunol. 2007; 37:2378-2389). In this DMH screen, CCR6 turned out be among the differentially methylated genes. The preferred differentially methylated region is located upstream of two reported CCR6 transcripts and overlaps with a putative CCR6 promoter (FIG. 1A). To confirm the DMH data the inventors performed bisulfite sequencing using genomic DNA from conventional naive CD45RA$^+$CD4$^+$ T cells and CD25$^{high}$CD4$^+$ Tregs isolated from human peripheral blood. CD25$^{high}$CD4$^+$ Tregs showed a largely demethylated CCR6 region (average methylation 23.8%), whereas conventional naive T cells were almost fully methylated (average methylation 81%) (FIG. 1B).

Figure 2:
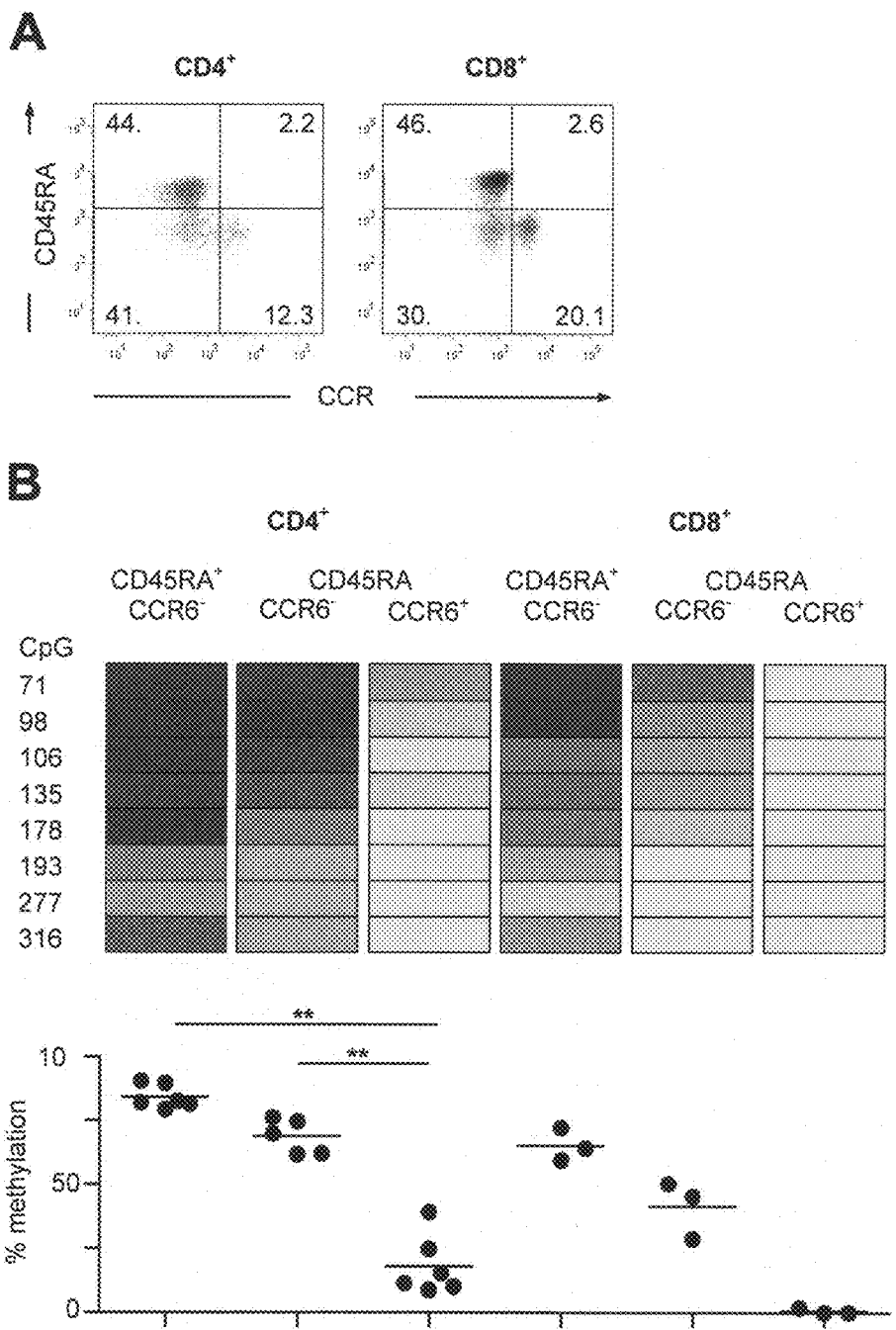
FIG. 2 shows that demethylation of the preferred CCR6 region correlates with CCR6 expression in human CD4 and CD8 cells. A) Representative FACS-staining of CCR6 and CD45RA on CD4$^+$CD25$^-$ and CD8$^+$CD25$^-$ lymphocytes. B) CD4$^+$ and CD8$^+$ cells were isolated from PBMC and sorted into CCR6$^-$ naive and CCR6$^-$ and CCR6$^+$ memory cells resulting in subsets with a purity>95%. Methylation analyses of sorted subsets are shown for one representative donor. Graphs below show the mean of methylation from CpG sites from five to six donors for CD4$^+$ T cells and three donors for CD8$^+$ T cells, respectively.

In addition to Tregs (Kleinewietfeld M, Puentes F, Borsellino G, Battistini L, Rotzschke O, Falk K. CCR6 expression defines regulatory effector/memory-like cells within the CD25+CD4+ T-cell subset. Blood. 2005; 105:2877-2886.) expression of CCR6 has been reported for both CD4$^+$ and CD8$^+$ memory T cells. In order to understand whether the observed demethylation of the CCR6 locus is confined to the fraction of cells that express CCR6 ex vivo, CD4$^+$ and CD8$^+$ T cell subsets were sorted according to CCR6 and CD45RA expression (FIG. 2A) and analyzed by bisulfite sequencing of the CCR6 locus. Both naive CD45RA'CD4$^+$ T cells lacking CCR6 expression as well as CCR6$^-$CD45RA$^-$CD4$^+$ memory T cells were strongly methylated, whereas CCR6-expressing CD4$^+$ memory T cells showed an almost complete demethylation of the analyzed CCR6 region (FIG. 2B). Although CD8$^+$ T cells displayed an overall lower level of DNA methylation, CCR6$^+$CD8$^+$ memory T cells clearly displayed a less methylated CCR6 region when compared to CCR6$^-$CD8$^+$ memory T cells (FIG. 2B). In accordance with these data, peripheral blood leukocyte subsets lacking CCR6 expression, such as resting CD14$^+$ monocytes and CD15$^+$ granulocytes, displayed an almost completely methylated CCR6 region (average methylation >84%), whereas CCR6-expressing CD56$^+$ NK and NKT cells and mature B cells were fully demethylated at this site. Together, the inventors' data show that CCR6 expression correlates with demethylation of the CCR6 region in human leukocytes.

CCR6$^+$ T Cells Stably Express CCR6 Upon In Vitro Expansion and Maintain a Demethylated CCR6 Region.

In order to investigate if both CCR6 expression on CD4$^+$ memory T cells and the corresponding methylation pattern of the analyzed CCR6 region were stable upon cell division, sorted CCR6$^+$CD25$^-$CD45RA$^-$CD4$^+$ T cells were labeled with CFSE and either stimulated with cytokines that mediate homeostatic turnover of memory cells or by triggering via the TCR. Consistent with previous reports (Geginat J, Sallusto F, Lanzavecchia A. Cytokine-driven proliferation and differentiation of human naive, central memory, and effector memory CD4(+) T cells. J Exp Med. 2001; 194:1711-1719), memory T cells proliferated in the presence of homeostatic cytokines such as IL-7 and IL-15, and all proliferating cells maintained high levels of CCR6 expression even after multiple cell divisions (FIG. 3A). TCR stimulation resulted in a down-regulation of CCR6 expression (Sallusto F, Kremmer E, Palermo B, et al. Switch in chemokine receptor expression upon TCR stimulation reveals novel homing potential for recently activated T cells. Eur J Immunol. 1999; 29:2037-2045), which was inhibited by TGF-β and promoted by IL-4 (FIGS. 3A and B). However, under all stimulation conditions tested the methylation status of the CCR6 region remained unchanged and showed a comparable low level of methylation (FIG. 3C). Importantly, TCR-induced down-regulation of CCR6 expression was only transient, since CCR6$^{-/low}$ cells that had lost CCR6 expression upon TCR stimulation rapidly re-expressed CCR6 after culture in the absence of TCR stimulation (FIG. 3D). Thus, demethylation of the CCR6 region is linked to long-term stability of CCR6 expression.

In Vitro Induction of CCR6 Expression is Unstable and does not Lead to Demethylation of the CCR6 Region.

Figure 4:
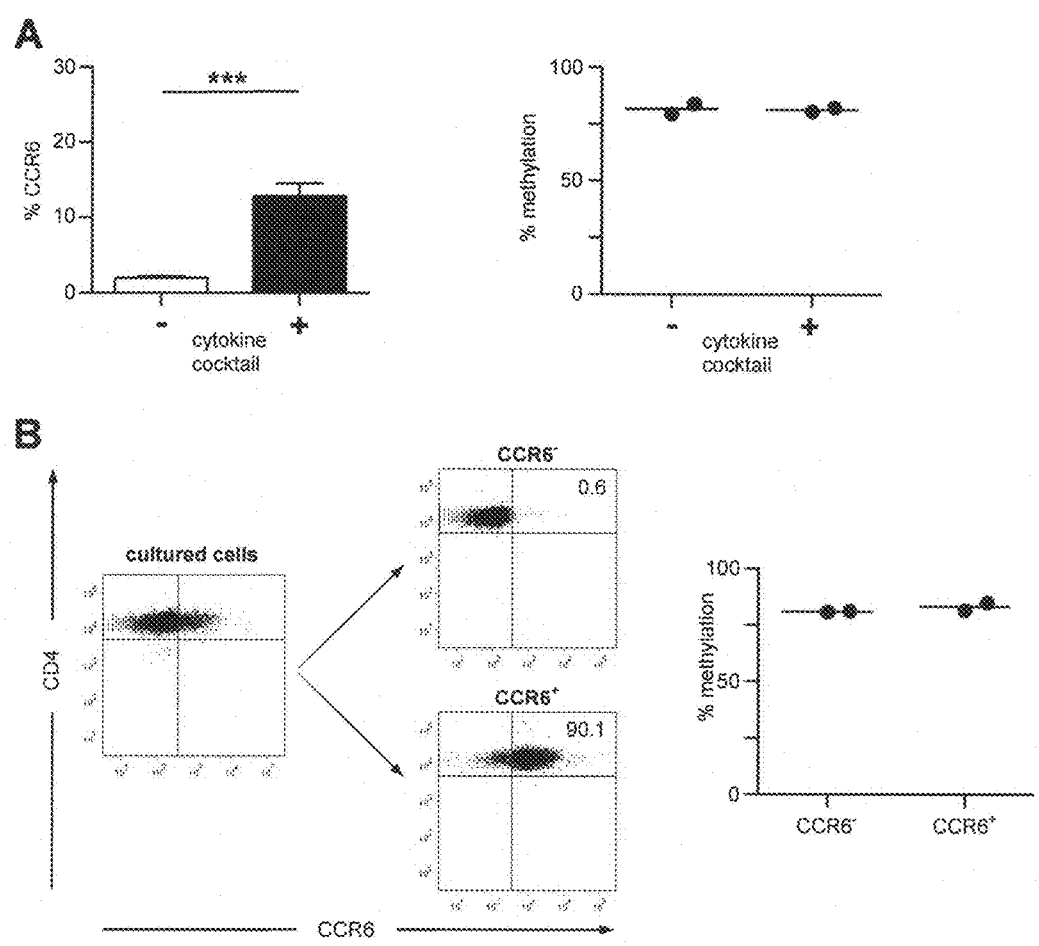
FIG. 4 shows that in vitro induced CCR6 is unstable and does not lead to demethylation of the preferred CCR6 region. A) Naive CD4+ T cells were stimulated without (white bars) or with proinflammatory cytokines and TGF-β (black bars) for four days, followed by culture in IL-2 (1000 U/ml). After six to seven days, cells were analyzed for CCR6 expression (n=21, left graph). The methylation profile of CD4+ T cells cultured with (+) and without (−) cytokine cocktail is shown in the right graph (n=2). B) Cells stimulated with the cytokine cocktail as in A were sorted into CCR6+ and CCR6− cells (shown for one representative donor) and analyzed for methylation of the CCR6 region. C) CCR6 expression (above) and methylation analysis (below) of the CCR6 region after stimulation as shown in D (one representative donor). D) Naive CD4+ T cells were cultured as in A and as shown in the left panel analyzed for CCR6 expression on day 7, 10 and 24 (n=4) or as depicted in the right panel restimulated after six to seven days under the same conditions as in the first stimulation and analyzed for CCR6 expression (n=11).
Figure 4:
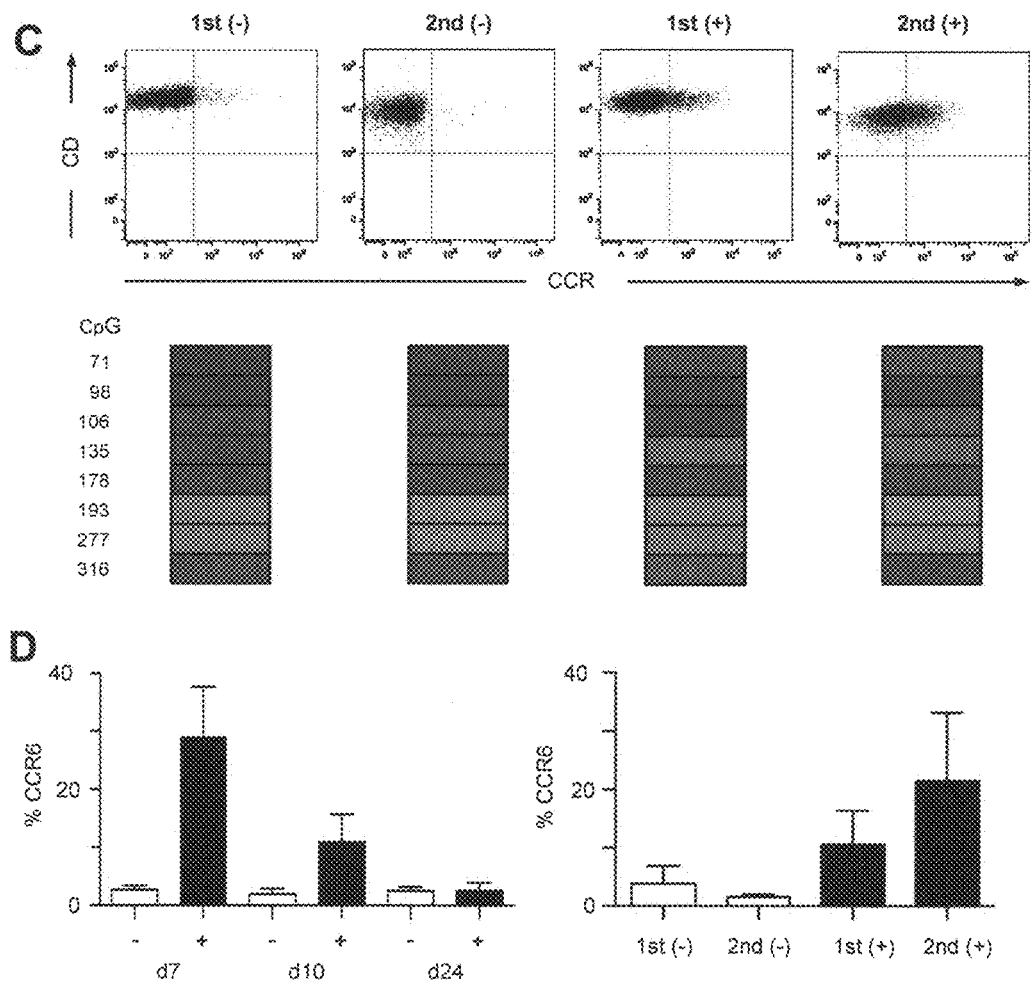

CCR6 expression can be induced in vitro on a fraction of naive CD4$^+$ T cells upon activation in presence of a cocktail of inflammatory cytokines (TNF-α, IL-6, IL-1) plus TGF-β. The inventors analyzed whether this de novo induction of CCR6 expression is associated with a demethylation of the CCR6 region. Naive CD4$^+$ T cells were stimulated with anti-CD3/anti-CD28 Dynabeads® in the presence of inflammatory cytokines and TGF-β. At day 6 of in vitro culture, a significantly higher fraction of T cells expressed CCR6 when compared to T cells stimulated in the absence of cytokines (FIG. 4A). However, both cell populations were almost completely methylated within the CCR6 region, showing no differences to unstimulated naive T cells (FIGS. 1B and 2B). Even after sorting into CCR6$^-$ and CCR6$^+$ cells, no selective demethylation of the CCR6 region could be observed within de novo induced CCR6$^+$ cells (FIG. 4B). Although repetitive stimulation in the presence of the cytokine cocktail further increased the frequency of CCR6$^+$ cells, demethylation of the CCR6 region was still not detectable (FIGS. 4C and 4D), showing that the cocktail of inflammatory cytokines was only sufficient to induce CCR6 expression, but not demethylation of the CCR6 locus. In contrast to ex vivo isolated CD4$^+$ memory T cells, CCR6 de novo induction in naive T cells by TCR stimulation in the presence of inflammatory cytokines led only to transient CCR6 expression, and virtually all cells lost CCR6 expression upon prolonged in vitro culture in the absence of the inducing cytokines (FIG. 4D).

Inhibition of DNA Methylation Leads to a Partially Stable CCR6 Expression in Cultivated Naive T Cells.

Figure 5:
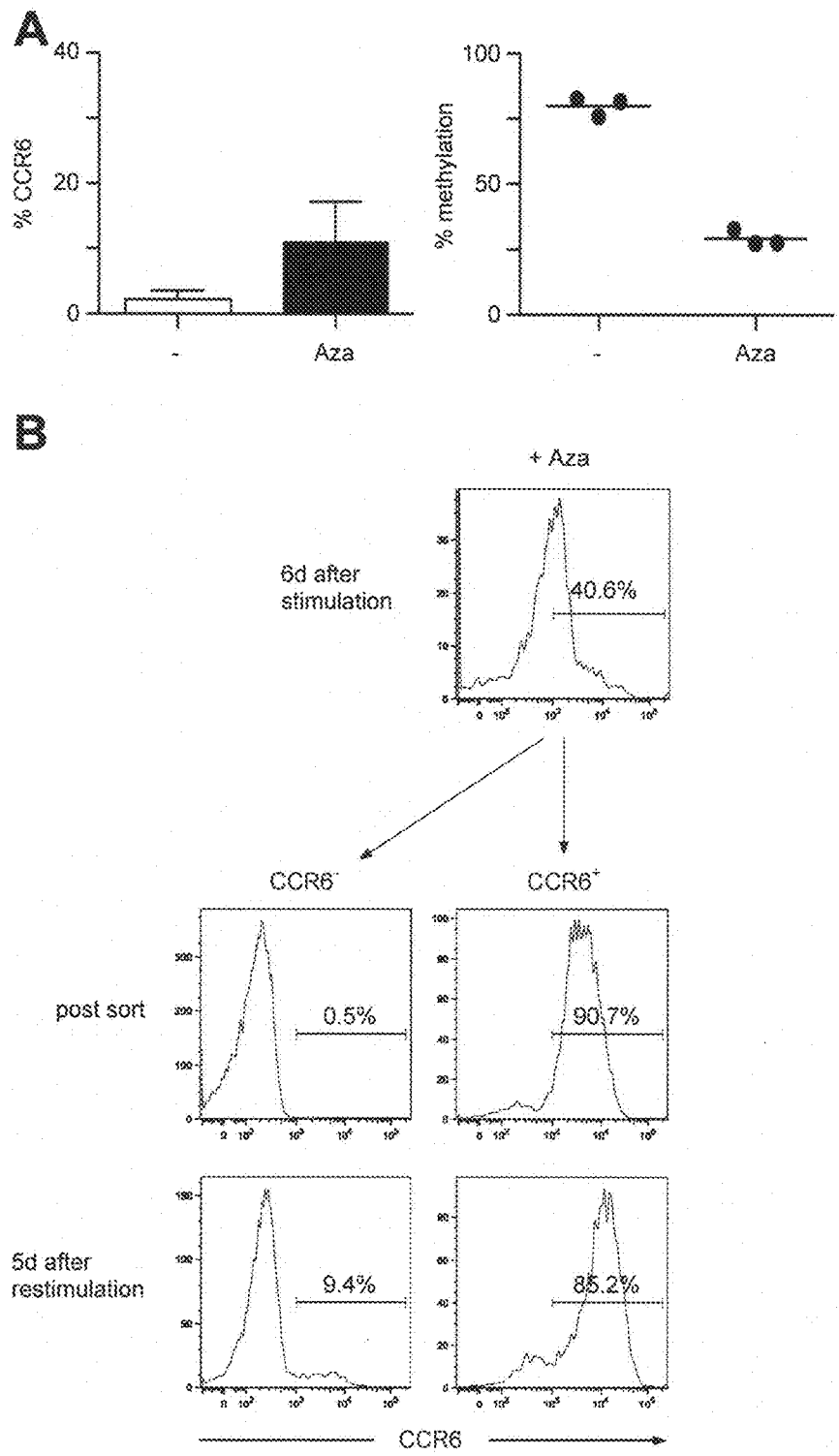
FIG. 5 shows that inhibition of DNA methylation leads to a partially stable CCR6 expression. A) Naive CD4+ T cells were stimulated without (n=18, left panel) or with (n=6, right panel) proinflammatory cytokines and TGF-β. After 48 h, Aza was added to the media for another 48 hours. Expression of CCR6 was analyzed on day 6. B) Naive CD4+ T cells were stimulated with Aza and without cytokines as in A. After six days, cells were sorted according to their CCR6 expression and restimulated under neutral conditions in the absence of Aza for additional five days followed by reanalysis of CCR6 expression. Data shown are representative for two independently performed experiments.

The DNA methylation status can be pharmacologically manipulated by induction of DNA replication in the presence of DNA-methyltransferase inhibitors such as 5'-azacytidine (Aza). To further investigate whether demethylation of the analyzed CCR6 region is involved in the stabilization of CCR6 expression, the inventors activated naive CD4$^+$ T cells with anti-CD3 and anti-CD28 Dynabeads® in the presence of Aza. Strikingly, Aza-treatment induced CCR6 expression in a significant fraction of cells even in the absence of exogenous cytokines, and in these Aza-treated cells a clear demethylation of the CCR6 region could be detected (FIG. 5A). Interestingly, when Aza-induced CCR6$^+$ cells were sorted and restimulated under neutral conditions in the absence of Aza, a remarkable stability of CCR6 expression was observed in these cells, showing further that demethylation of the CCR6 locus controls stable chemokine receptor expression in T cells.

The Differentially Methylated Element of the CCR6 Locus Harbors Transcriptional Activity.

The preferred differential methylated region of the CCR6 locus is located 444/446 bases upstream of two predicted CCR6 transcripts (FIG. 1A). The CCR6 region partially overlaps with an in silico predicted promoter region. Promoter-typical elements like a transcriptional start site were not detected in the CCR6 region, but putative binding sites for the transcriptional regulators PPAR, GATA, AHR, ETS1 or RXR, some of them, e.g. ETS1, binding in a methylation-dependent manner to their target sequences (Maier H, Colbert J, Fitzsimmons D, Clark D R, Hagman J. Activation of the early B-cell-specific mb-1 (Ig-alpha) gene by Pax-5 is dependent on an unmethylated Ets binding site. Mol Cell Biol. 2003; 23:1946-1960, and own unpublished observations).

To analyze the role of the CCR6 region for the transcriptional regulation of CCR6 expression, the inventors cloned this element into a luciferase reporter vector, which contains a SV40 minimal promoter, allowing the detection of transcriptionally active enhancer elements. Upon transfection into total CD4$^+$ T cells isolated from peripheral blood, transcriptional activity of the CCR6 region containing luciferase reporter construct was increased about 2.4 fold compared to the empty control vector (FIG. 6). Interestingly, the transcriptional activity of the CCR6 region was independent of the activation status of the cells since stimulation of the transfected CD4$^+$ T cells with PMA plus ionomycin led to comparable results. These findings demonstrate that the differentially methylated region of the CCR6 locus displays enhancer activity independently of TCR-mediated signals, suggesting that this element is functionally involved in the maintenance of stable CCR6 expression in memory T cells.

Example 2

Different T cell species were purified and FACS sorted from two independent donors. The separated the cells using CD4 and CD8 as markers for the segregation of cytotoxic and helper T cells. Then, these populations were further separated into naïve and memory cell populations by employing CD45RA. Memory populations were further separated into CCR6 positive and CCR6 negative populations. The results are summarized in the following table 1.

TABLE 1

Figure 8A:
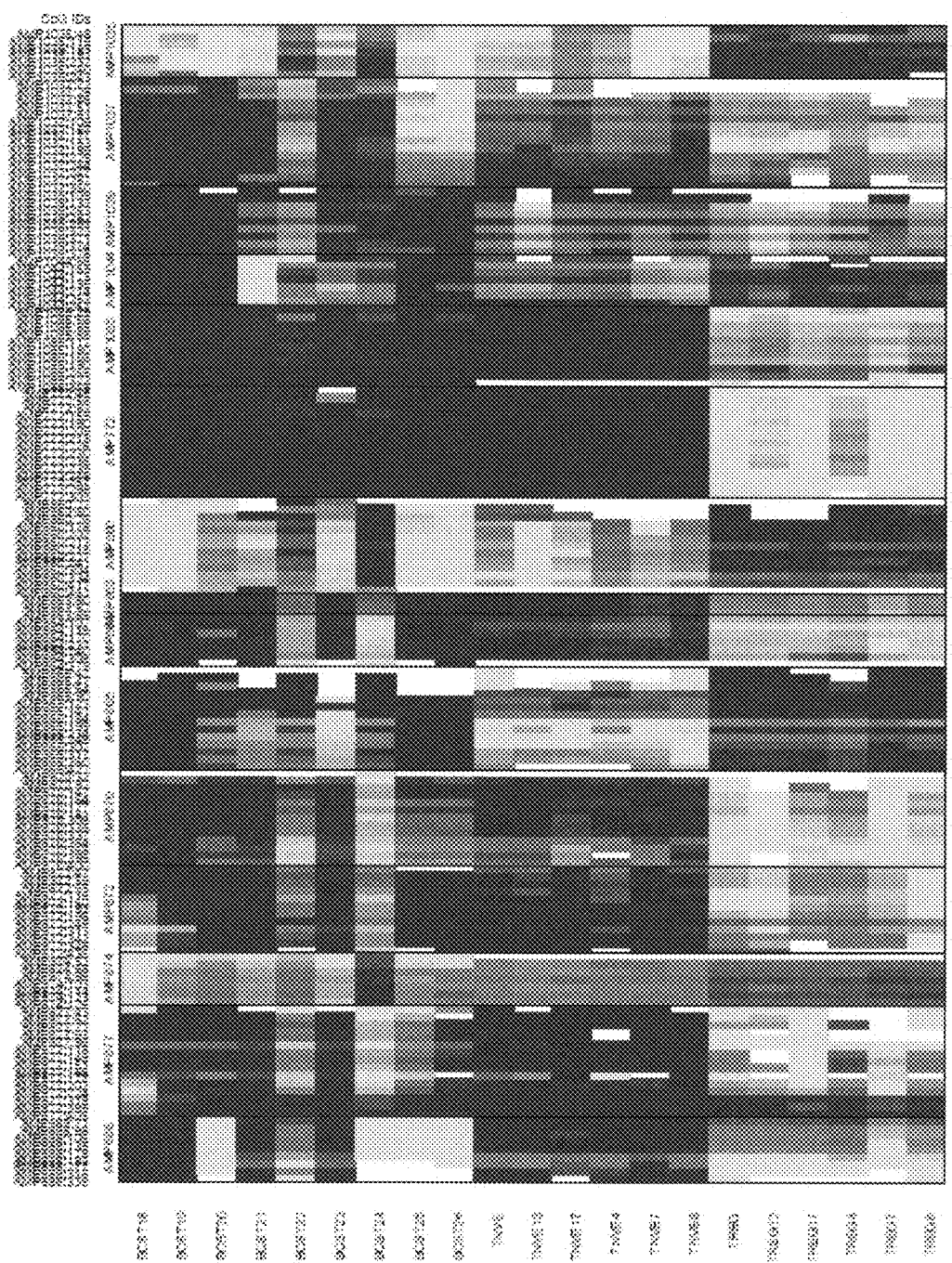
FIG. 8A shows the methylation of particular CpG positions in the promoter of the CCR6 and BLR1 gene in different leukocyte cell types (BCST18: granulocytes; BCST19: monocytes; BCST20: NK cells; BCST21: nave T-cells; BCST22: memory T-cells; BCST23: naïve cytotoxic T-cells; BCST24: memory cytotoxic T-cells; BCST25: naïve B-cells; BCST26: memory B-cells). Particular positions in the amplicon are indicated by the number following the amplicon, i.e. AMP888:71 is position 71 in amplicon 888. Starting from CpG 178 in Amp 888 down to CpG71 strictly cell type dependent methylation can be observed. Naïve T cells, regardless their expression status of CD4 and CD8 show increased methylation. In contrast CCR6 sorted memory T cells do segregate into intermediate to fully methylated fraction, defined by the non-CCR6 expressing fraction and the CCR6 expressing fraction, which at the same time is fully demethylated at the measured locus. A high degree of methylation in BLR1 (amplicon 1037) can be found in granulocytes, monocytes, NK cells, naïve T-cells, naïve cytotoxic T-cells, and memory cytotoxic T-cells.
Figure 8B:
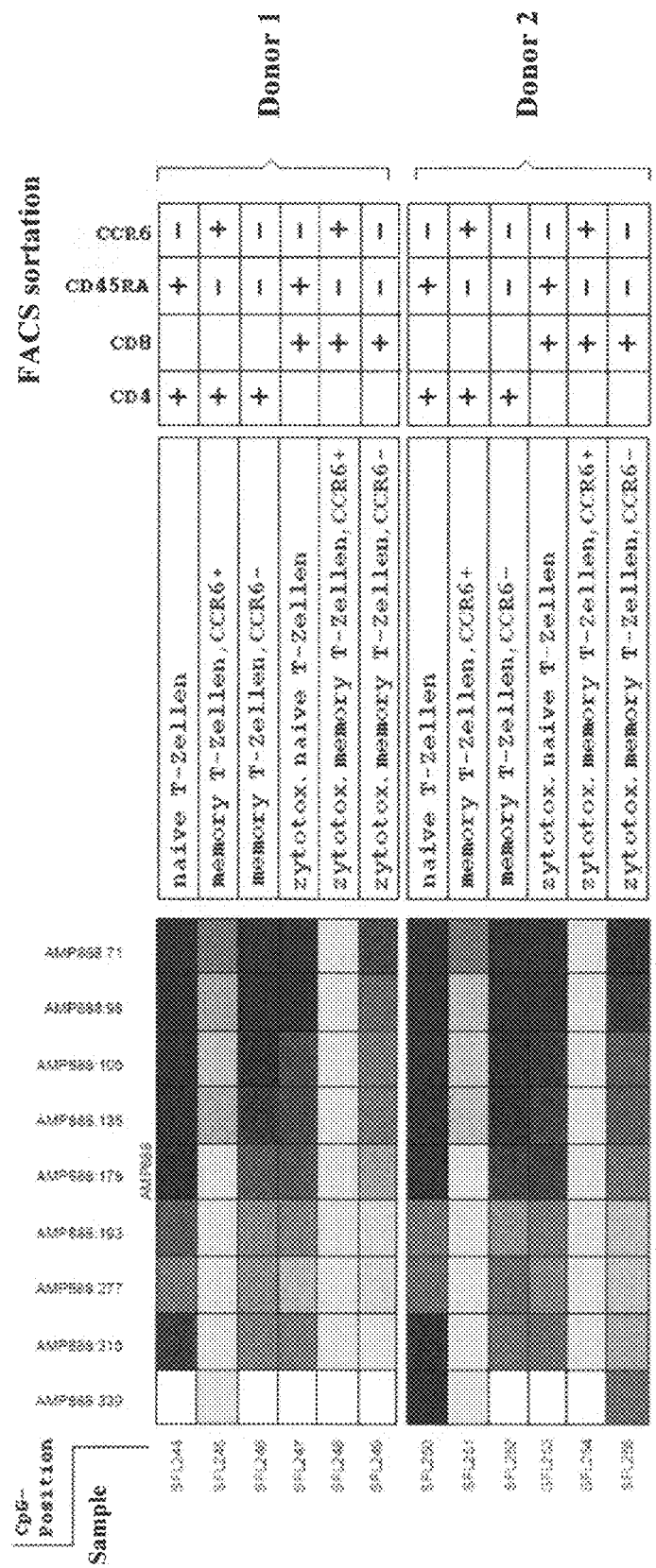
FIG. 8B shows the methylation of particular CpG positions in the promoter of the CCR6 gene in different leukocyte cell types in different donors. It can be observed that the methylation status is donor independent.
Figure 10:
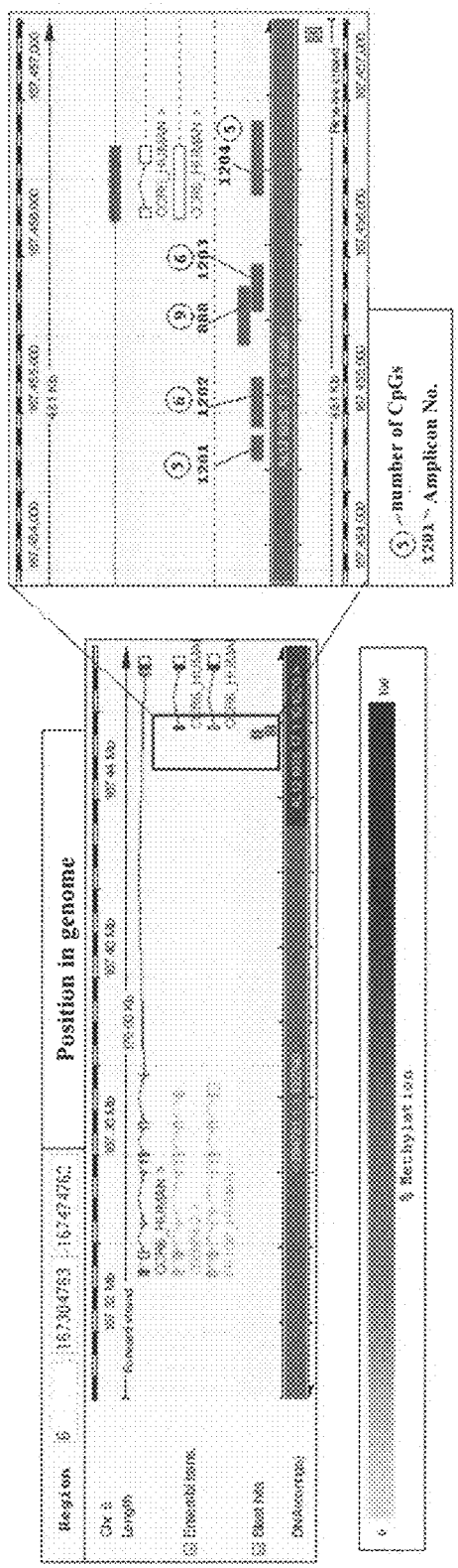
FIG. 10 shows the various analysed amplicons shown in FIGS. 1 and 2, when plotted on chromosome 6 in the human genome. The amplicons are shown and the number of CpGs per amplicon are indicated in the circles.

Methylation pattern of the genes according to the invention (see FIG. 8)

| Cell type | Methylation BLR-1 (Amplicon 1037), FIG. 8 | Methylation CCR-6 (Amplicon 888), FIG. 8 |
|---|---|---|
| Granulocytes | + | + |
| Monocytes | + | + |
| NK-cells | − | − |
| Naïve T-cells | + | + |
| Memory T-cells | − | − |

TABLE 1-continued

Methylation pattern of the genes according to the invention (see FIG. 8)

| Cell type | Methylation BLR-1 (Amplicon 1037), FIG. 8 | Methylation CCR-6 (Amplicon 888), FIG. 8 |
|---|---|---|
| Naïve cytotoxic T-cells | + | + |
| Memory cytotoxic T-cells | − | − |
| Naïve B-cells | − | − |
| Memory B-cells | − | − |

Figure 11:
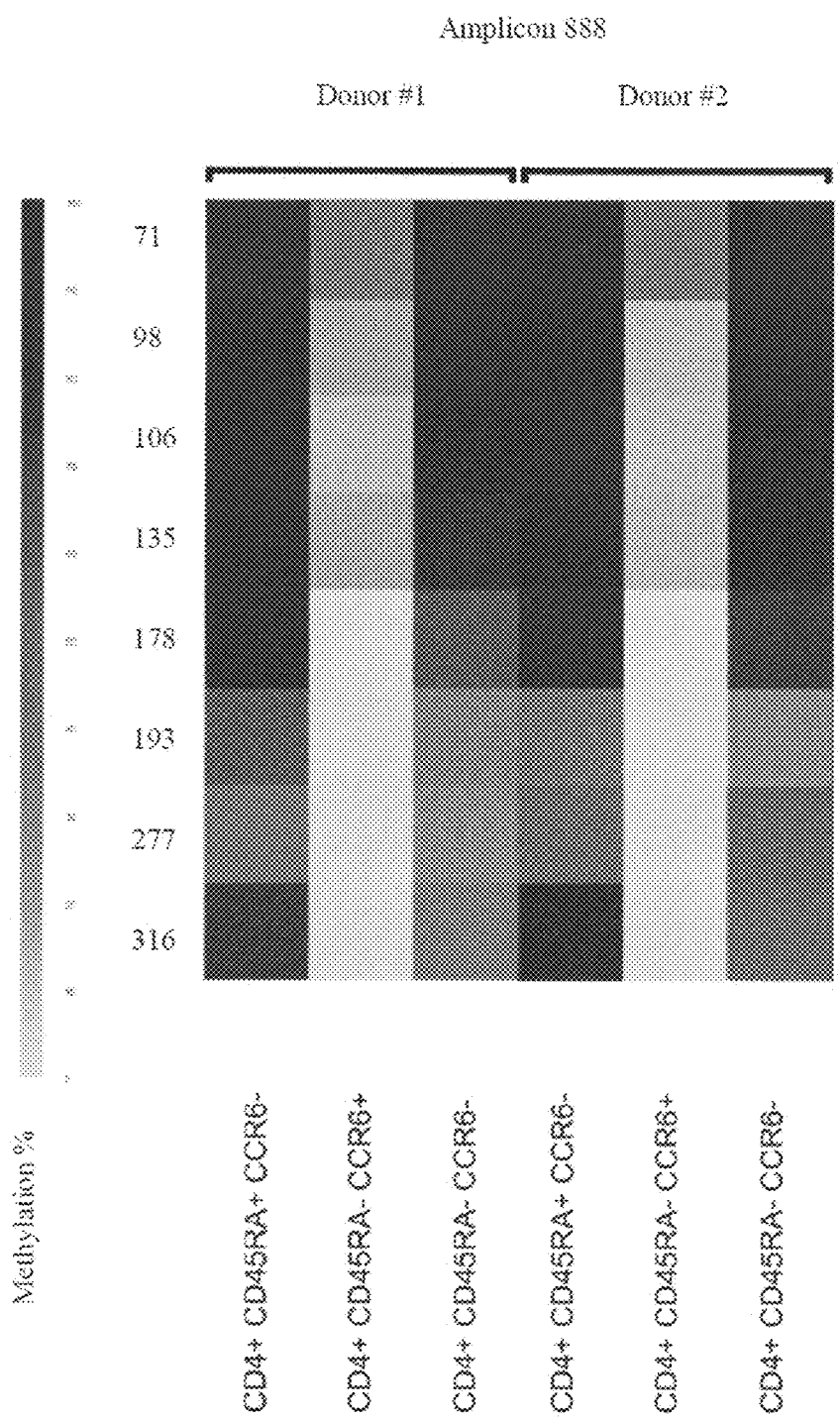
FIG. 11 shows the reproducibility of DNA methylation pattern (amplicon 888) for CCR6 that were analyzed from two donors and sorted into CD4+CD45RA+ and CD4+CD45RA−. Each column represents one blood cell subset with each row representing a single CpG site (position in the amplicon indicated on the left). DNA methylation was measured by means of bisulfite sequencing. CpG methylation levels (left bar) are color coded according to the color scale ranging from light gray (0% methylation) to dark gray (100% methylation).
Figure 12:
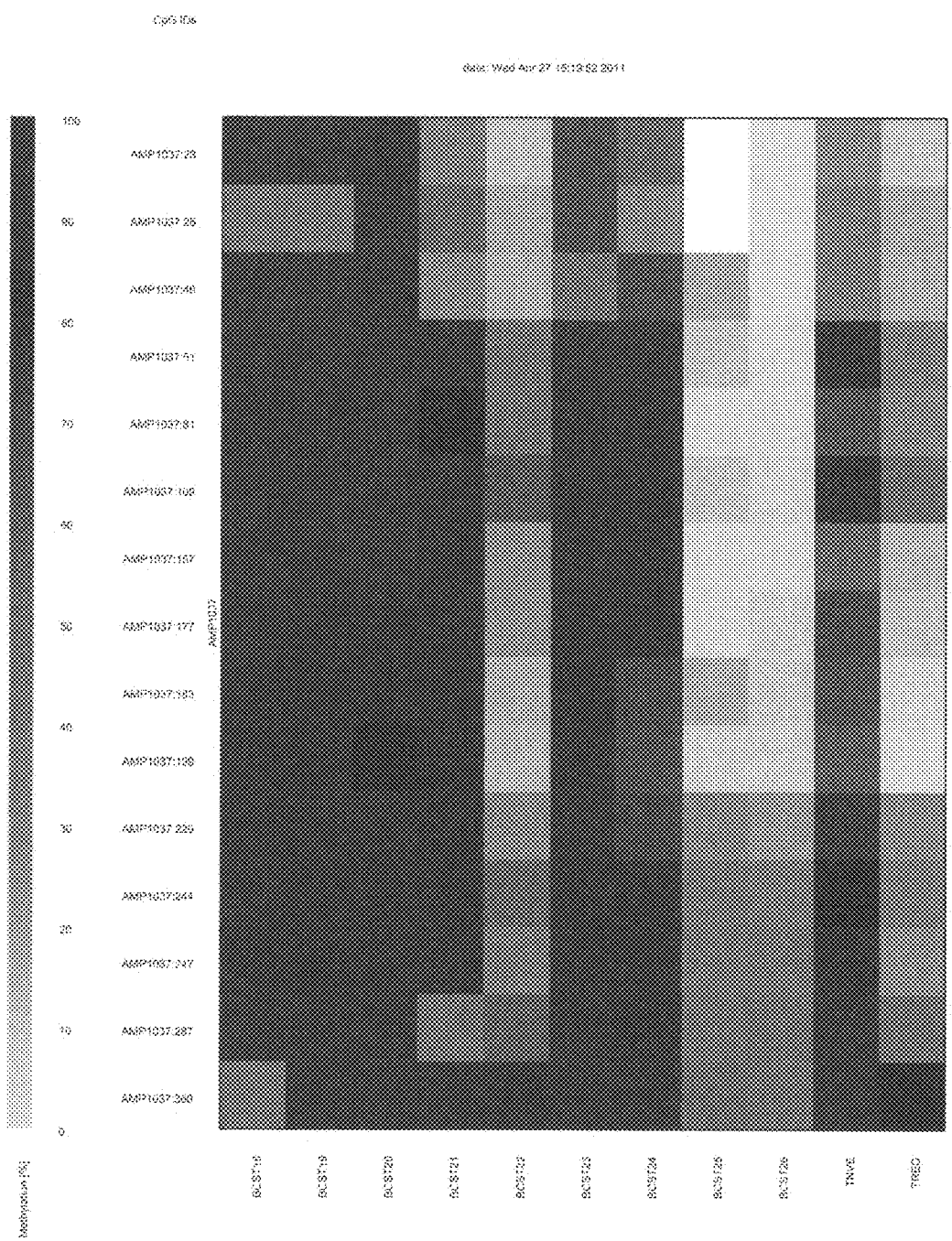
FIG. 12 shows the methylation level of particular CpG positions in the promoter region of the BLR1 gene in different leukocyte cell types (BCST18: granulocytes; BCST19: monocytes; BCST20: NK cells; BCST21: naïve T-helper cells; BCST22: memory T-helper cells; BCST23: naïve cytotoxic T-cells; BCST24: memory cytotoxic T-cells; BCST25: naïve B-cells; BCST26: memory B-cells; TNVE; naïve T-helper cells; Treg regulatory T cells). Particular positions in the amplicon are indicated by the number following the amplicon, i.e. AMP1037:23 is position 23 in amplicon 1037. Starting from CpG 23 in Amp 1037 up to CpG 360 a strictly cell type dependent methylation can be observed. A high degree of methylation in BLR1 (amplicon 1037) can be found in granulocytes, monocytes, NK cells, naïve T-helper cells, naïve cytotoxic T-cells, and memory cytotoxic T-cells. A low degree of methylation can be found in memory T-helper cells, memory and naïve B-cells and regulatory T cells.

The samples were further subjected to a qPCR analysis directed to CCR6 CpG positions 71, 98, 106 and 135 in amplicon 888 in order to confirm the bisulfite sequencing data shown in FIG. 11. The methylation specific (specific to "CpG") primer pair used is shown in SEQ ID No. 14/15, the corresponding probe is shown in SEQ ID No. 16; for detecting de-methylated sequences (specific to "TpG") the primer pair shown in SEQ ID No. 17/18 was used in connection with probe SEQ ID No. 19. The results are summarized in Table 2. The bisulfite sequencing results shown in FIG. 11 could be confirmed in the qPCR assay.

TABLE 2 shows the DNA methylation pattern (amplicon 888) for CCR6 that were analyzed from two donors and sorted into CD4$^+$CD45RA$^+$ and CD4$^+$CD45RA$^-$

| Samples Description | specific to "TpG" | | | specific to "CpG" | | | Data Analysis Mode: 2$^{nd}$ Derivative | |
|---|---|---|---|---|---|---|---|---|
| | CP | S.D. | Copy Number | CP | S.D. | Copy Number | | |
| 12,500 Copies | 25.29 | 0.02 | 13968.04 | 25.65 | 0.03 | 12676.28 | "TpG". | "CpG". |
| 2,500 Copies | 27.92 | 0.01 | 2265.25 | 28.00 | 0.01 | 2583.61 | [%] | [%] |
| 500 Copies | 30.27 | 0.15 | 449.02 | 30.33 | 0.09 | 532.49 | | |
| 100 Copies | 32.55 | 0.09 | 92.37 | 33.15 | 0.01 | 78.44 | De- | Methyl. |
| 20 Copies | 34.61 | 0.03 | 22.26 | 34.89 | 0.23 | 24.33 | Methyl. | |
| CD4+CD45RA+CCR6− Donor #1 | 33.95 | 0.50 | 36.44 | 27.15 | 0.18 | 4615.12 | 0.8 | 99.2 |
| CD4+CD45RA−CCR6+ Donor #1 | 27.24 | 0.38 | 3697.32 | 27.92 | 0.16 | 2721.32 | 57.6 | 42.4 |
| CD4+CD45RA−CCR6− Donor #1 | 31.21 | 0.45 | 242.03 | 26.73 | 0.12 | 6126.05 | 3.8 | 96.2 |
| CD4+CD45RA+CCR6− Donor #2 | 33.84 | 0.32 | 38.41 | 26.47 | 0.24 | 7338.90 | 0.5 | 99.5 |
| CD4+CD45RA−CCR6+ Donor #2 | 29.07 | 0.24 | 1039.11 | 29.59 | 0.06 | 873.96 | 54.3 | 45.7 |
| CD4+CD45RA−CCR6− Donor #2 | 34.50 | 0.23 | 24.11 | 27.67 | 0.10 | 3228.76 | 0.7 | 99.3 |

The invention claimed is:

1. A method for identifying an immune cell in a sample, obtained from a human, as an NK-cell, CCR6$^+$ memory T-cell, B-cell, granulocyte, monocyte, or naïve T-cell, wherein said method comprises the steps of:
   a) obtaining said sample, comprising said immune cell, from said human, wherein the immune cells in the sample consist of the following types: NK-cell, CCR6$^+$ memory T-cell, B-cell, granulocyte, monocyte, or naïve T cell,
   b) performing a nucleic acid based assay on said immune cell to determine the methylation status of at least one CpG position in the gene ccr6 in an amplicon as amplified by a primer pair of SEQ ID NOs: 1 and 2, wherein the methylation status of the at least one CpG position in said amplicon is determined by a method comprising bisulfite treating the genomic DNA isolated from the immune cell and amplifying said amplicon by said primer pair of SEQ ID NOs: 1 and 2, and
   c) identifying said immune cell as the NK-cell, CCR6$^+$ memory T-cell, or B-cell based on the at least one CpG position in said amplicon being CpG position 71, 98, 106, 135, 178, 193, or 316 and being less than 20% methylated, as determined in step b), or identifying the immune cell as the granulocyte, monocyte, or naïve T-cell based on the at least one CpG position in said amplicon being CpG position 71, 98, 106, 135, or 178 and being at least 80% methylated as determined in step b).

2. The method according to claim 1, wherein said at least one CpG position is the CpG position 71 in said amplicon.

3. The method of claim 1, wherein the CCR6$^+$ memory T cell is a CCR6$^+$ memory cytotoxic T cell and the naïve T-cell is a naïve cytotoxic T-cell.

4. A method for identifying a sample of immune cells obtained from a human as containing a type of immune cells at the purity of at least 95%, wherein the type of immune cells is selected from the group consisting of NK-cells, CCR6$^+$ memory T-cells, B-cells, granulocytes, monocytes, and naïve T-cells, and wherein said method comprises the steps of:
   a) obtaining said sample comprising said immune cells from said human, wherein the immune cells in the sample consist of the following types: NK-cells, CCR6+ memory T-cells, B-cells, granulocytes, monocytes, and naïve T-cells,
   b) performing a nucleic acid based assay on said sample of immune cells to determine the methylation status of at least one CpG position in the gene ccr6 in an amplicon as amplified by a primer pair of SEQ ID NO: 1 and 2, wherein the methylation status of the at least one CpG position in said amplicon is determined by a method comprising bisulfite treating the genomic DNA isolated from the immune cell and amplifying said amplicon by said primer pair of SEQ ID NO: 1 and 2, and
   c) identifying said sample as containing a type of immune cells selected from the group consisting of NK-cells, CCR6$^+$ memory T-cells, and B-cells at the purity of at least 95% based on the at least one CpG position in said amplicon being CpG position 71, 98, 106, 135, 178, 193, or 316 and being less than 20% methylated as determined in step b), or identifying said sample as containing a type of immune cells selected from the group consisting of granulocytes, monocytes, and naïve T-cells at the purity of at least 95% based on the at least one CpG position in said amplicon being CpG position 71, 98, 106, 135, or 178 and being at least 80% methylated as determined in step b).

5. The method according to claim 4, wherein said at least one CpG position is the CpG position 71 in said amplicon.

6. The method of claim 4, wherein the CCR6$^+$ memory T cell is a CCR6$^+$ memory cytotoxic T cell and the naïve T-cell is a naïve cytotoxic T-cell.

* * * * *

UNITED STATES PATENT AND TRADEMARK OFFICE
CERTIFICATE OF CORRECTION

PATENT NO. : 9,783,846 B2
APPLICATION NO. : 13/636556
DATED : October 10, 2017
INVENTOR(S) : Sven Olek It is certified that error appears in the above-identified patent and that said Letters Patent is hereby corrected as shown below:

In the Specification

Column 6,
Line 54, "CCR6-" should read -- CCR6⁻ --.

Column 16,
Line 59, "TGF - 13" should read -- TGF - β --.

Column 20,
Line 12, "M/uI and Bg1II" should read -- *Mlu*I and *Bgl*II --.

Column 22,
Lines 12-17,
"GCCAGTGGGGTTGAGCAGGACACAGGTCCTGCTGTGTCTAGCTGGTTCCCCA GAGAGATGATAAGGGGTGC<u>G</u>CTCCAGCTTCTCAGGCTCACTCAGGC<u>G</u>TGAGG AC<u>G</u>TGGAGCTCAGGGCTCTGCAGGAAGGAGC<u>G</u>ACCCAGGTGAGGTGTGGTC AA" should read
-- GCCAGTGGGGTTGAGCAGGACACAGGTCCTGCTGTGTCTAGCTGGTTCCCCA GAGAGATGATAAGGGGTGC<u>G</u>CTCCAGCTTCTCAGGCTCACTCAGGC<u>G</u>TG AGGAC<u>G</u>TGGAGCTCAGGGCTCTGCAGGAAGGAGC<u>G</u>ACCCAGGTGAGGT GTGGTCAA --.

Column 23,
Line 3, "CD45RA'CD4⁺ T cells" should read -- CD45RA⁺ CD4⁺ T cells --.

Signed and Sealed this
Fifth Day of June, 2018

Andrei Iancu
*Director of the United States Patent and Trademark Office*

SEQUENCE LISTING

<160> NUMBER OF SEQ ID NOS: 29

<210> SEQ ID NO 1
<211> LENGTH: 22
<212> TYPE: DNA
<213> ORGANISM: Homo sapiens

<400> SEQUENCE: 1
gttagtgggg ttgagtagga ta                                        22

<210> SEQ ID NO 2
<211> LENGTH: 23
<212> TYPE: DNA
<213> ORGANISM: Homo sapiens

<400> SEQUENCE: 2
aaaaccctaa aatcacaaaa cta                                       23

<210> SEQ ID NO 3
<211> LENGTH: 22
<212> TYPE: DNA
<213> ORGANISM: Homo sapiens

<400> SEQUENCE: 3
ttggtaatgt ttgtttggaa ag                                    22

<210> SEQ ID NO 4
<211> LENGTH: 22
<212> TYPE: DNA
<213> ORGANISM: Homo sapiens

<400> SEQUENCE: 4
ctcctaaatc cctcaacatc ta                                    22

<210> SEQ ID NO 5
<211> LENGTH: 22
<212> TYPE: DNA
<213> ORGANISM: Homo sapiens

<400> SEQUENCE: 5
aaactcacaa cttccttcac tc                                    22

<210> SEQ ID NO 6
<211> LENGTH: 23
<212> TYPE: DNA
<213> ORGANISM: Homo sapiens

<400> SEQUENCE: 6
aagggtagtg ttagagggta ttt                                   23

<210> SEQ ID NO 7
<211> LENGTH: 25
<212> TYPE: DNA
<213> ORGANISM: Homo sapiens

<400> SEQUENCE: 7
cacctaatct tcatataaca caaaa                                 25

<210> SEQ ID NO 8
<211> LENGTH: 22
<212> TYPE: DNA
<213> ORGANISM: Homo sapiens

<400> SEQUENCE: 8
ggtatagtgt attgggaagt gg                                    22

<210> SEQ ID NO 9
<211> LENGTH: 24
<212> TYPE: DNA
<213> ORGANISM: Homo sapiens

<400> SEQUENCE: 9
ccttatctac ttcttccaca aaat                                  24

<210> SEQ ID NO 10
<211> LENGTH: 22
<212> TYPE: DNA
<213> ORGANISM: Homo sapiens

<400> SEQUENCE: 10

```
agtgatgagt tgtgaggtag gt                                          22

<210> SEQ ID NO 11
<211> LENGTH: 29
<212> TYPE: DNA
<213> ORGANISM: Homo sapiens

<400> SEQUENCE: 11
gactacgcgt cagtaagggg gagccactg                                   29

<210> SEQ ID NO 12
<211> LENGTH: 29
<212> TYPE: DNA
<213> ORGANISM: Homo sapiens

<400> SEQUENCE: 12
gactagatct caaggaaagc agctgacga                                   29

<210> SEQ ID NO 13
<211> LENGTH: 365
<212> TYPE: DNA
<213> ORGANISM: Homo sapiens

<400> SEQUENCE: 13
gccagtgggg ttgagcagga cacaggtcct gctgtgtcta gctggttccc cagagagatg    60 ataagggtg cgctccagct tctcaggctc actcaggcgt gaggacgtgg agctcagggc   120
tctgcaggaa ggagcgaccc aggtgaggtg tggtcaagat agagcagagc tgggcagcgg   180
gcagtggagc ctcgtgggca gcctgggggt ggggaggcac agtgcactgg gaagtggaga   240
aagtgtgagt ccatcaggct ggctgagaat tgatcacgaa cctattgtct gtaaaacttt   300
tgttatttcc tgagacgtgg ttcacagcaa cccaggtgcg aacagccttg tgattctagg   360
gttct                                                              365

<210> SEQ ID NO 14
<211> LENGTH: 17
<212> TYPE: DNA
<213> ORGANISM: Homo sapiens

<400> SEQUENCE: 14
gagatgataa ggggtgc                                                 17

<210> SEQ ID NO 15
<211> LENGTH: 17
<212> TYPE: DNA
<213> ORGANISM: Homo sapiens

<400> SEQUENCE: 15
acacctcacc taaatcg                                                 17

<210> SEQ ID NO 16
<211> LENGTH: 23
<212> TYPE: DNA
<213> ORGANISM: Homo sapiens

<400> SEQUENCE: 16
tttaggcgtg aggacgtgga gtt                                          23

<210> SEQ ID NO 17
<211> LENGTH: 17
<212> TYPE: DNA
<213> ORGANISM: Homo sapiens
```

```
<400> SEQUENCE: 17
gagatgataa ggggtgt                                                    17

<210> SEQ ID NO 18
<211> LENGTH: 20
<212> TYPE: DNA
<213> ORGANISM: Homo sapiens

<400> SEQUENCE: 18
accacacctc acctaaatca                                                 20

<210> SEQ ID NO 19
<211> LENGTH: 29
<212> TYPE: DNA
<213> ORGANISM: Homo sapiens

<400> SEQUENCE: 19
atttaggtgt gaggatgtgg agtttaggg                                       29

<210> SEQ ID NO 20
<211> LENGTH: 17
<212> TYPE: DNA
<213> ORGANISM: Homo sapiens

<400> SEQUENCE: 20
gagatgataa ggggtgc                                                    17

<210> SEQ ID NO 21
<211> LENGTH: 17
<212> TYPE: DNA
<213> ORGANISM: Homo sapiens

<400> SEQUENCE: 21
acacctcacc taaatcg                                                    17

<210> SEQ ID NO 22
<211> LENGTH: 23
<212> TYPE: DNA
<213> ORGANISM: Homo sapiens

<400> SEQUENCE: 22
tttaggcgtg aggacgtgga gtt                                             23

<210> SEQ ID NO 23
<211> LENGTH: 17
<212> TYPE: DNA
<213> ORGANISM: Homo sapiens

<400> SEQUENCE: 23
gagatgataa ggggtgt                                                    17

<210> SEQ ID NO 24
<211> LENGTH: 20
<212> TYPE: DNA
<213> ORGANISM: Homo sapiens

<400> SEQUENCE: 24
accacacctc acctaaatca                                                 20

<210> SEQ ID NO 25
<211> LENGTH: 29
<212> TYPE: DNA
```

<213> ORGANISM: Homo sapiens

<400> SEQUENCE: 25

| atttaggtgt gaggatgtgg agtttaggg | 29 |

<210> SEQ ID NO 26
<211> LENGTH: 463
<212> TYPE: DNA
<213> ORGANISM: Homo sapiens

<400> SEQUENCE: 26

| tctcttttc ttatcacttt accattggtt ggactttgat tccagggatc ctacgattac | 60 |
| tcaataccct acaggatata catggttaac catttgcatt tgggcaaata ggcgttactt | 120 |
| ttcaatagga agtggcaatc cagaacttgc ttttgggcaa ttctagtagc tcaccgcttt | 180 |
| tttcttaatg actgctagaa gctgcatctt attgacagat ggtcatcaca ttggtgagct | 240 |
| ggagtcatca gattgtgggg cccggagtga ggctgaaggg agtggatcag agcactgcct | 300 |
| gaggtgagca tgccaaggcc cctgagactt ttctttcaaa aatgtaactt ctttgatccc | 360 |
| ctagtctgac aggaatggga ctgttttact cattaatctt ccagaatgct ggcatattga | 420 |
| ccatgtttat gcttaacgac acagacttcc tttcctgaaa gca | 463 |

<210> SEQ ID NO 27
<211> LENGTH: 24
<212> TYPE: DNA
<213> ORGANISM: Homo sapiens

<400> SEQUENCE: 27

| tctcttttc ttatcacttt acca | 24 |

<210> SEQ ID NO 28
<211> LENGTH: 22
<212> TYPE: DNA
<213> ORGANISM: Homo sapiens

<400> SEQUENCE: 28

| tgtttttagg aaaggaagtt tg | 22 |

<210> SEQ ID NO 29
<211> LENGTH: 406
<212> TYPE: DNA
<213> ORGANISM: Homo sapiens

<400> SEQUENCE: 29

| agtgatgagt tgtgaggcag gtcgcggccc tactgcctca ggagacgatg cgcagctcat | 60 |
| ttgcttaaat ttgcagctga cggctgccac ctctctagag gcacctggcg gggagcctct | 120 |
| caacataaga cagtgaccag tctggtgact cacagccggc acagccatga actacccgct | 180 |
| aacgctggaa atggacctcg agaacctgga ggacctggtg agtagacacg ggtagcttcc | 240 |
| tgtcgccgag gccctgtctg gaattctaac atcctttgcc agagtccgag ggagagggga | 300 |
| cagtgtggga atcctctccc actgtggatc tgtaaaatct agacaggtca gtcagctccc | 360 |
| gcccttaag agtttatttt ccattctgtg gaagaagcag ataagg | 406 |